US011207408B2

(12) United States Patent
Piergallini et al.

(10) Patent No.: US 11,207,408 B2
(45) Date of Patent: Dec. 28, 2021

(54) BIOPHOTONIC COMPOSITIONS, METHODS, AND KITS FOR INHIBITING AND DISRUPTING BIOFILMS

(71) Applicant: KLOX TECHNOLOGIES INC., Laval (CA)

(72) Inventors: Remigio Piergallini, San Benedetto del Tronto (IT); Nikolaos Loupis, Athens (GR); David Ohayon, Dollard-des-Ormeaux (CA); Kevin Wilkinson, Laval (CA); Giovanni Scapagnini, Catania (IT)

(73) Assignee: KLOX TECHNOLOGIES INC., Laval (CA)

( * ) Notice: Subject to any disclaimer, the term of this patent is extended or adjusted under 35 U.S.C. 154(b) by 213 days.

(21) Appl. No.: 16/333,873

(22) PCT Filed: Sep. 22, 2017

(86) PCT No.: PCT/CA2017/051123
§ 371 (c)(1),
(2) Date: Mar. 15, 2019

(87) PCT Pub. No.: WO2018/053646
PCT Pub. Date: Mar. 29, 2018

(65) Prior Publication Data
US 2019/0209683 A1 Jul. 11, 2019

Related U.S. Application Data

(60) Provisional application No. 62/399,225, filed on Sep. 23, 2016.

(51) Int. Cl.
| | | |
|---|---|---|
| *A61K 41/00* | (2020.01) | |
| *A61P 31/04* | (2006.01) | |
| *A61N 5/06* | (2006.01) | |
| *A61P 31/00* | (2006.01) | |
| *A61P 31/10* | (2006.01) | |
| *A61K 9/00* | (2006.01) | |
| *A61K 31/365* | (2006.01) | |

(52) U.S. Cl.
CPC ............ *A61K 41/00* (2013.01); *A61K 9/0014* (2013.01); *A61K 31/365* (2013.01); *A61N 5/06* (2013.01); *A61N 5/0624* (2013.01); *A61P 31/00* (2018.01); *A61P 31/04* (2018.01); *A61P 31/10* (2018.01); *A61N 5/062* (2013.01); *A61N 2005/0661* (2013.01)

(58) Field of Classification Search
None
See application file for complete search history.

(56) References Cited

FOREIGN PATENT DOCUMENTS

| | | |
|---|---|---|
| CA | 2948258 A1 | 1/2011 |
| WO | 2002089750 A2 | 11/2002 |
| WO | 2005034790 A2 | 4/2005 |
| WO | 2009052638 A1 | 4/2009 |
| WO | 2010051636 A1 | 5/2010 |
| WO | 2010051641 A1 | 5/2010 |
| WO | 2010070292 A1 | 6/2010 |
| WO | 2011006253 A1 | 1/2011 |
| WO | 2011084744 A1 | 7/2011 |
| WO | 2013155620 A1 | 10/2013 |
| WO | 2014040176 A1 | 3/2014 |
| WO | 2015000058 A1 | 1/2015 |
| WO | WO-2017017631 A2 * | 2/2017 ........... C07D 471/00 |

OTHER PUBLICATIONS

Brock et al., "Use of In Vitro and In Vivo Data in the Design, Development, and Quality Control of Sustained-Release Decongestant Dosage Forms", Pharmacotherapy, vol. 14, No. 4, 1994.
Deleon et al., "Synergistic Interactions of Pseudomonas aeruginosa and *Staphylococcus aureaus* in an In Vitro Wound Model", Infection and Immunity, Nov. 2014, vol. 82, No. 11, pp. 4718-4728.
Durrani et al., "Studies on Drugs Release Kinetics From Carbopol® 934P Tablets", Pharmaceutical Res. Supp. 8: S-135, 1991—abstract only.
Harper et al., "Bacteriophages and Biofilms", Antibiotics (Basel), Sep. 2014, vol. 3, No. 3, pp. 270-284.
Lavery et al., "The efficacy and safety of Grafix® for the treatment of chronic diabetic foot ulcers: results of a multi-centre, controlled, randomised, blinded, clinical trial", International Wound Journal, 2014, 11, 554-560.
Zhang et al., "Quantifying Diffusion in a Biofilm of *Streptococcus mutans*", Antimicrobial Agents and Chemotherapy, Mar. 2011, vol. 55, No. 3, pp. 1075-1081.
National Pressure Ulcer Panel (NPUAP) and the European Pressure Ulcer Advisory Panel (EPUAP), Pressure Ulcer Treatment, Quick reference guide 2009. Available at: http://www.npuap.org.
European Search Report and opinion issued from the European Patent Office dated Apr. 14, 2020, in corresponding application 17852043.3.
Nikolis et al., "A prospective case series evaluating the safety and efficacy of the Klox BioPhotonic System in venous leg ulcers", Chronic Wound Care Management and Research, vol. 3, Sep. 15, 2016, pp. 101-111, XP055681902.
Biel, "Photodynamic therapy of bacterial and fungal biofilm infections", in Photodynamic Therapy: Methods and Protocols, Methods and Molecular Biology, Gomer, C.J. (ed.), 2010, 635, Chapter 13, pp. 175-194.
Biel, "Antimicrobial photodynamic therapy for treatment of biofilm-based infections", in Biofilm-based Healthcare-associated infections: vol. II, Advanced in Experimental Medicine and Biology, Donelli, G. (ed.), 2015, Chapter 8, pp. 119-136.

(Continued)

*Primary Examiner* — Zinna Northington Davis
(74) *Attorney, Agent, or Firm* — BCF LLP

(57) ABSTRACT

The present document describes methods of using compositions for inhibiting biofilm formation, or disrupting existing or developing biofilms in a subject, which composition comprises at least one chromophore and a pharmacologically acceptable carrier.

19 Claims, 2 Drawing Sheets

(56) References Cited

OTHER PUBLICATIONS

De Melo et al., "Photodynamic inactivation of biofilm: Taking a lightly colored approach to stubborn infection", Expert Review of Anti-Infective Therapy, 2013, 11(7), 669-693.
Cieplik et al., "Antimicrobial photodynamic therapy for inactivation of biofilms formed by oral key pathogens", Frontiers in Microbiology, 2014, 5, Article 405.
Barra et al., "Photodynamic and antibiotic therapy in combination to fight biofilms and resistant surface bacterial infections". International Journal of Molecular Sciences, 2015, 16, 20417-20430.
Freire et al., "Comparison of the effects of rose bengal-and eosin Y-mediated photodynamic inactivation of planktonic cells and biofilms of Candida albicans", Lasers in Medical Science, 2014, 29, 949-955.
Wood et al., "Erythrosine is a potential photosensitizer for the photodynamic therapy of oral plaque biofilms". Journal of Antimicrobial Chemotherapy, 2006, 57, 680-684.
Biel et al., "Antimicrobial photodynamic therapy treatment of chronic recurrent sinusitis biofilms", International Forum of Allergy and Rhinology, 2011, 1(5), 329-334.
Goulart et al., "Comparative study of methylene blue and erythrosine dyes employed in photodynamic therapy for inactivation of planktonic and biofilm-cultivated Aggregatibacter antinomycetemcomitans", Photomedicine and Laser Surgery, 2010, 28(S1), S85-S90.
Vilela et al., "Photodynamic inactivation of *Staphyloccocus aureus* and *Escherichia coli* biofilm by malchite green and phenothiazine dyes: An in vitro study", Archives of Oral Biology, 2012, 57, 704-710.
Araujo et al., "Photodynamic antimicrobial therapy of curcumin in biofilms and carious dentine", Lasers in Medical Science, 2014, 29, 629-635.
Stojicic et al., "Ex vivo killing of Enterococcus faecalis and mixed plaque bacteria in planktonic and biofilm culture by modified photoactivated disinfection", International Endodontic Journal, 2013, 46, 649-659.
Gopalakrishnan et al., "Photodynamic therapy in controlling biofilm—A novel therapeutic approach", Indian Journal of Dental Advancements, 2011, 3(S1), 732-736.
Sadekuzzaman et al., "Current and recent advanced strategies for combinating biofilms". Comprehensive Reviews in Food Science and Food Safety, 2015, 14, 491-509.
Dong et al., "Distribution and Inhibition of Liposomes on *Staphylococcus aureus* and Pseudomonas aeruginosa Biofilm", PLoS ONE 10(6): e0131806. https://doi.org/10.1371/journal.pone.0131806, Published Jun. 30, 2015.
Javanbakht et al., "Relating the Surface Properties of Superparamagnetic Iron Oxide Nanoparticles (SPIONs) to Their Bactericidal Effect towards a Biofilm of *Streptococcus mutans*", PLoS ONE 11(4): e0154445. https://doi.org/10.1371/journal.pone.0154445, Published Apr. 26, 2016.

\* cited by examiner

BIOPHOTONIC COMPOSITIONS, METHODS, AND KITS FOR INHIBITING AND DISRUPTING BIOFILMS

TECHNICAL FIELD

This description relates to the field of inhibiting biofilm formation or disrupting existing or developing biofilms in a subject. Said biofilms could be associated with skin or soft tissues in a medical condition.

BACKGROUND

Biofilms are mucilaginous communities of microorganisms such as bacteria, archaea, fungi, molds, algae or protozoa or mixtures thereof that grow on various surfaces. Biofilms form when microorganisms establish themselves on a surface and activate genes involved in producing a matrix that includes polysaccharides. This matrix may provide protection of biofilm forming bacteria from biocides.

Biofilms can be formed by different microorganism species and genera including bacteria, archaea, fungi, molds, algae or protozoa or mixtures thereof that grow on various surfaces. Current therapies to treat tissue-related biofilms include debridement, systemic antibiotics, topical agents, and bacteriophages. Debridement of wounds is performed to mechanically remove and disperse the biofilm. Based on the severity of wounds, simple tools such as curette or ultrasound energy are used to disrupt the biofilm matrix. While this technique may disrupt the ECM of the biofilm, it will not prevent further growth of bacteria in the wound. Thus, treatment of tissue-related biofilms often combines debridement of wounds with other antimicrobial treatments.

Systemic antibiotics are used as a systemic, systems-wide treatment of the biofilm and may prevent further growth of bacteria on the wound surface. While systemic antibiotics may retard biofilm growth to an extent, elimination of the microorganisms forming the biofilm would require antibiotics at 500-1000 times the level that can be achieved using systemic antibiotics. Thus, topical antibiotic treatment has been the standard of care for biofilms.

Topical agents such as antibiotic creams, silver, cadexomer iodine, and methylene blue are topically applied to treat the biofilm. The advantage of using topical antibiotics to treat biofilms is that the concentration used on the biofilm is much higher than that which can be achieved using systemic antibiotics. However, the inability of topical antibiotics to penetrate through the biofilm matrix is a key factor in the antibiotic resistance commonly found in biofilms.

While strong antimicrobial agents may kill bacteria at the surface of the biofilm, bacteria at the center of the biofilm, which are protected by the matrix, might be illuminated with a low or non-lethal concentration of antimicrobial agents. It has been well documented that the penetration rates of antibiotics through biofilms are dependent not only on the bacterial species forming the biofilm, but also on the antibiotic used. Agents that help antimicrobials penetrate the biofilm's surface layer will improve the effectiveness of the antimicrobials. Another factor explaining the high resistance rate of biofilms to antibiotics is due to the dense, low-oxygen environment created by biofilms. The low-oxygen levels result in decreased metabolic activity, and stagnated growth rates of bacteria. Since many antibiotics such as β-lactam antibiotics are only toxic against actively growing bacteria, the decreased growth rate contributes to antibiotic resistance.

There is, therefore, an ongoing need to identify agents, compositions and methods for inhibiting biofilm formation or disrupting existing or developing biofilms. The biophotonic therapy of the disclosure provides new methods for inhibiting biofilm formation or disrupting existing or developing biofilms, such as biofilms related to skin or soft tissues or biofilms associated with a medical condition in a subject, such as wounds.

SUMMARY OF THE INVENTION

The present disclosure describes methods, compositions, kits, and uses for inhibiting biofilm formation, disrupting existing biofilms, disrupting developing biofilms, and/or breaking down biofilms, such as those found in wounds, skin, or soft tissues of a subject. In some embodiments, the biofilm comprises *Staphylococcus aureus* and/or *Pseudomonas aeruginosa*. In some embodiments, the biofilm is produced by a microorganism such as bacteria, yeast, or fungi. A subject in need can apply any composition as described herein directly to the area of biofilm.

In one aspect, this disclosure describes a method for inhibiting biofilm formation or disrupting existing or developing biofilms in a subject, comprising: a) topically applying a composition comprising at least one chromophore and a pharmaceutically acceptable carrier; and b) illuminating said composition with actinic light, thereby inhibiting biofilm formation or disrupting existing or developing biofilms in the subject. In certain aspects, the composition is a biophotonic composition. In certain such aspects, the composition is a topical biophotonic composition. In some aspects, the biofilms are formed from single or mixed bacterial species.

In one aspect, this disclosure describes a method for inhibiting biofilm formation or disrupting existing or developing biofilms in a subject suffering from venous leg ulcer (VLU), comprising: a) topically applying a composition comprising at least one chromophore and a pharmaceutically acceptable carrier; and b) illuminating said composition with actinic light, thereby inhibiting biofilm formation or disrupting existing or developing biofilms in the subject. In certain aspects, the composition is a biophotonic composition. In certain such aspects, the composition is a topical biophotonic composition. In some aspects, the biofilms are formed from single or mixed bacterial species.

In one aspect, this disclosure describes a method for inhibiting biofilm formation or disrupting existing or developing biofilms in a subject suffering from diabetic foot ulcer (DFU), comprising: a) topically applying a composition comprising at least one chromophore and a pharmaceutically acceptable carrier; and b) illuminating said composition with actinic light, thereby inhibiting biofilm formation or disrupting existing or developing biofilms in the subject. In certain aspects, the composition is a biophotonic composition. In certain such aspects, the composition is a topical biophotonic composition. In some aspects, the biofilms are formed from single or mixed bacterial species.

In one aspect, this disclosure describes a method for inhibiting biofilm formation or disrupting existing or developing biofilms in a subject suffering from pressure ulcer (PU), comprising: a) topically applying a composition comprising at least one chromophore and a pharmaceutically acceptable carrier; and b) illuminating said composition with actinic light, thereby inhibiting biofilm formation or disrupting existing or developing biofilms in the subject. In certain aspects, the composition is a biophotonic composition. In certain such aspects, the composition is a topical biophotonic composition. In some aspects, the biofilms are formed from single or mixed bacterial species.

In some embodiments of any of the foregoing or following, said composition is illuminated with actinic light for a period of less than about 9 minutes, e.g., for a period of from about 1 second to about 8 minutes, from about 1 minute to about 8 minutes, from about 2 minutes to about 7 minutes, from about 3 minutes to about 6 minutes, from about 4 minutes to about 5 minutes. In certain embodiments, said composition is illuminated with actinic light for a period of less than about 5 minutes per $cm^2$ of an area to be treated, e.g., for a period of from about 1 second to about 5 minutes per $cm^2$.

In some embodiments of any of the foregoing or following, the source of actinic light is placed over an area of biofilm. In some embodiments, said actinic light is visible light having a wavelength between about 400 nm and about 700 nm.

In some embodiments of any of the foregoing or following, the chromophore of the composition is chosen from a xanthene derivative dye, an azo dye, a biological stain, and a carotenoid. In certain such embodiments, said xanthene derivative dye is chosen from a fluorene dye (e.g., a pyronine dye, such as pyronine Y or pyronine B, or a rhodamine dye, such as rhodamine B, rhodamine G, or rhodamine WT), a fluorone dye (e.g., fluorescein, or fluorescein derivatives, such as phloxine B, rose bengal, merbromine, Eosin Y, Eosin B, or Erythrosine B), or a rhodole dye. In certain such embodiments, said azo dye is chosen from methyl violet, neutral red, para red, amaranth, carmoisine, allura red AC, tartrazine, orange G, ponceau 4R, methyl red, and murexide-ammonium purpurate. In certain such embodiments, said biological stain is chosen from safranin O, basic fuchsin, acid fuschin, 3,3' dihexylocarbocyanine iodide, carminic acid, and indocyanine green. In certain such embodiments, said carotenoid is chosen from crocetin, a-crocin (S,S-diapo-S,S-carotenoic acid), zeaxanthine, lycopene, α-carotene, β-carotene, bixin, and fucoxanthine. In certain such embodiments, said carotenoid is present in the composition as a mixture chosen from saffron red powder, annatto extract, and brown algae extract.

In some embodiments of any of the foregoing or following, the composition further comprises at least one oxidant. In certain such embodiments, the oxidant is chosen from hydrogen peroxide, carbamide peroxide and benzoyl peroxide. In other embodiments, the oxidant is chosen from a peroxy acid and an alkali metal percarbonate.

In some embodiments of any of the foregoing or following, this disclosure provides a method for inhibiting biofilm formation or disrupting existing or developing biofilms in a subject, comprising topically applying a composition comprising at least one oxidant and chromophore; and illuminating said composition with actinic light to cause photoillumination of the composition. In certain embodiments, the composition is a biophotonic composition. In certain such embodiments, the composition is a topical biophotonic composition.

In some embodiments of any of the foregoing or following, the composition further comprises at least one healing factor, e.g., hyaluronic acid, glucosamine, or allantoin.

In certain aspects of the disclosure, said composition does not comprise the presence of an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In certain embodiments of any of the foregoing or following, the composition further comprises one or more salts selected from the group consisting of one or more bicarbonate salts, one or more carbonate salts, and a combination of the foregoing salts.

In certain aspects, the disclosure provides a method for inhibiting biofilm formation or disrupting existing or developing biofilms in a subject, comprising topically applying a composition, said composition comprising at least one chromophore; at least one salt selected from the group consisting of one or more bicarbonate salts, one or more carbonate salts, and a combination of the foregoing salts; and a pharmaceutically acceptable carrier; and illuminating said composition to actinic light to cause photoillumination of the composition. In certain aspects, the composition is biophotonic a composition. In certain such aspects, the composition is a topical biophotonic composition.

In certain aspects, the disclosure provides a method for inhibiting biofilm formation or disrupting existing or developing biofilms in a subject suffering from venous leg ulcer (VLU), comprising topically applying a composition, said composition comprising at least one chromophore; at least one salt selected from the group consisting of one or more bicarbonate salts, one or more carbonate salts, and a combination of the foregoing salts; and a pharmaceutically acceptable carrier; and illuminating said composition to actinic light to cause photoillumination of the composition. In certain aspects, the composition is biophotonic a composition. In certain such aspects, the composition is a topical biophotonic composition.

In certain aspects, the disclosure provides a method for inhibiting biofilm formation or disrupting existing or developing biofilms in a subject suffering from diabetic foot ulcer (DFU), comprising topically applying a composition, said composition comprising at least one chromophore; at least one salt selected from the group consisting of one or more bicarbonate salts, one or more carbonate salts, and a combination of the foregoing salts; and a pharmaceutically acceptable carrier; and illuminating said composition to actinic light to cause photoillumination of the composition. In certain aspects, the composition is biophotonic a composition. In certain such aspects, the composition is a topical biophotonic composition.

In certain aspects, the disclosure provides a method for inhibiting biofilm formation or disrupting existing or developing biofilms in a subject suffering from pressure ulcer (PU), comprising topically applying a composition, said composition comprising at least one chromophore; at least one salt selected from the group consisting of one or more bicarbonate salts, one or more carbonate salts, and a combination of the foregoing salts; and a pharmaceutically acceptable carrier; and illuminating said composition to actinic light to cause photoillumination of the composition. In certain aspects, the composition is biophotonic a composition. In certain such aspects, the composition is a topical biophotonic composition.

In some embodiments of any of the foregoing or following, the composition further comprises at least one gelling agent, e.g., glucose, modified starch, methyl cellulose, carboxymethyl cellulose, propyl cellulose, hydroxypropyl cellulose, a carbomer, alginic acid, sodium alginate, potassium alginate, ammonium alginate, calcium alginate, agar, carrageenan, locust bean gum, pectin, or gelatin.

In certain embodiments of any of the foregoing or following, said composition further comprises at least one buffering agent, such as an ethylenediaminetetraacetic acid (EDTA) or ethylene glycol tetraacetic acid (EGTA). In certain embodiments of any of the foregoing or following, the chelating agent is EDTA.

In some aspects, there is disclosed a use of a composition, e.g., a biophotonic composition, for the manufacture of a medicament for inhibiting biofilm formation or disrupting existing or developing biofilms in a subject, wherein the composition comprises at least one chromophore and a pharmaceutically acceptable carrier. In certain aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

In certain aspects, there is disclosed a use of a composition e.g., a biophotonic composition, for inhibiting biofilm formation or disrupting existing or developing biofilms in a subject, wherein the composition comprises at least one chromophore and a pharmaceutically acceptable carrier. In certain aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

In certain aspects, there is disclosed a use of a composition e.g., a biophotonic composition, for inhibiting biofilm formation or disrupting existing or developing biofilms in a subject having VLU, wherein the composition comprises at least one chromophore and a pharmaceutically acceptable carrier. In certain aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

In certain aspects, there is disclosed a use of a composition e.g., a biophotonic composition, for inhibiting biofilm formation or disrupting existing or developing biofilms in a subject having DFU, wherein the composition comprises at least one chromophore and a pharmaceutically acceptable carrier. In certain aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

In certain aspects, there is disclosed a use of a composition e.g., a biophotonic composition, for inhibiting biofilm formation or disrupting existing or developing biofilms in a subject having PU, wherein the composition comprises at least one chromophore and a pharmaceutically acceptable carrier. In certain aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

Definitions

Before continuing to describe the present disclosure in further detail, it is to be understood that this disclosure is not limited to specific compositions or process steps, as such may vary. It must be noted that, as used in this specification and the appended embodiments, the singular form "a", "an" and "the" include plural referents unless the context clearly dictates otherwise.

As used herein, the term "about" in the context of a given value or range refers to a value or range that is within 20%, within 10%, and more within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "biophotonic" as used herein refers to the generation, manipulation, detection and application of photons in a biologically relevant context. In other words, compositions exert their physiological effects primarily due to the generation and manipulation of photons.

The term "composition" is a composition as described herein that may be illuminated with light to induce a production of photons for biologically relevant applications.

The term "actinic light" is intended to mean light energy emitted from a specific light source (lamp, LED, or laser) and capable of being absorbed by matter (e.g. the chromophore defined below) and produce an identifiable or measurable change when it interacts with it; as clinically identifiable change we can presume a change in the color of the chromophore used (e.g. from red to transparent).

The term "topical" means as applied to body surfaces, such as the skin, mucous membranes, vagina, oral cavity, internal surgical wound sites, and the like.

The term "chromophore" refers to a compound which, when illuminated by light irradiation, is capable of absorbing the light.

The term "oxidant" as used herein refers to either a compound that readily transfers oxygen atoms and oxidizes other compounds, or a substance that gains electrons in a redox chemical reaction.

The term "chelating agent" as used herein refers to a compound that binds metal ions, such as iron, and facilitates their solvation in solution.

The term "healing factor" is intended to mean a compound that promotes or enhances the healing or regenerative process of a tissue.

The term "time of illumination to actinic light" is intended to mean the time a tissue, skin or wound is illuminated with actinic light per application of actinic light.

The term "total time of illumination to actinic light" is intended to mean the cumulative time a tissue, skin or wound is illuminated with actinic light after several application of actinic light.

The term "hydrophilic gelling agent" is intended to mean a material that thickens and stabilizes liquid solutions, emulsions, and suspensions. Hydrophillic gelling agents dissolve in liquid and provide a structure giving the resulting gel an appearance of a solid matter, while being mostly composed of a liquid. Hydrophillic gelling agents are very similar to thickeners.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
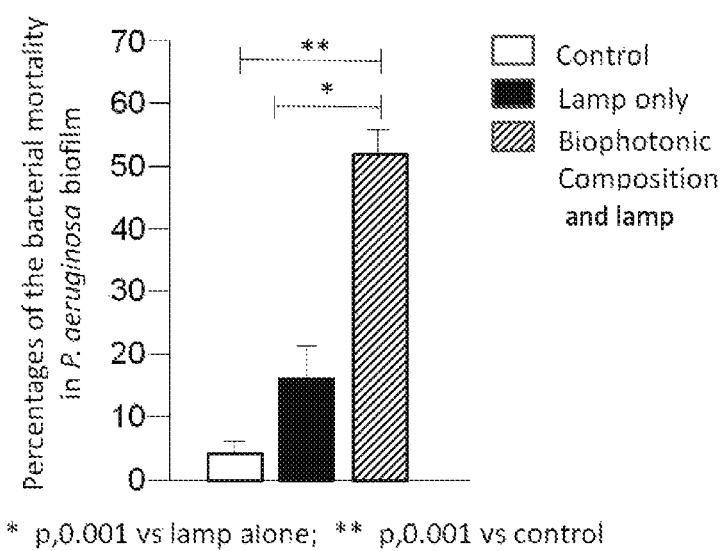
FIG. 1 shows results of the mortality of bacteria *P. aeruginosa* in a biofilm with treatment of a biophotonic composition as disclosed in this application. The *P. aeruginosa* biofilm was treated with a biophotonic composition illuminated in comparison to control composition or illumination alone (illumination in the presence of a composition lacking both the chromophore and oxidant).

In one aspect, this disclosure describes a method for inhibiting biofilm formation or disrupting existing or developing biofilms in a subject (e.g., a subject suffering from VLU, DFU, and/or PU), comprising: a) topically applying a composition comprising at least one chromophore and a pharmaceutically acceptable carrier; and b) illuminating said composition to actinic light to cause photoillumination of the composition. In certain embodiments, the composition is a biophotonic composition. In certain such embodiments, the composition is a topical biophotonic composition.

In certain embodiments of any of the foregoing or following, the chromophore is selected from the group consisting of a xanthene derivative dye, an azo dye, a biological stain, and a carotenoid. In certain such embodiments, the at least one chromophore is selected from the group consisting of eosin (e.g., eosin B or eosin Y), erythrosine (e.g., erythrosine B), and Saffron red powder.

In certain embodiments of any of the foregoing or following, the composition comprises at least one chromophore present in an amount of at least about 0.2% by weight of the composition, e.g., from about 0.02% to about 12%, from 0.02% to about 10%, from 0.02% to about 8%, from about 0.02% to about 6%, from about 0.02% to about 4%, from about 0.02% to about 2%, from about 0.02% to about 1%, or about 0.5% by weight of the composition.

In some embodiments of any of the foregoing or following, the composition further comprises an additional chromophore selected from the group consisting of Xanthene derivative dye, azo dye, biological stain, and carotenoid.

In some embodiments of any of the foregoing or following, the chromophore or chromophore of the composition is selected from the group consisting of a xanthene derivative dye, an azo dye, a biological stain, and a carotenoid. In certain such embodiments, said xanthene derivative dye is chosen from a fluorene dye (e.g., a pyronine dye, such as pyronine Y or pyronine B, or a rhodamine dye, such as rhodamine B, rhodamine G, or rhodamine WT), a fluorone dye (e.g., fluorescein, or fluorescein derivatives, such as phloxine B, rose bengal, merbromine, Eosin Y, Eosin B, or Erythrosine B), or a rhodole dye. In certain such embodiments, said azo dye is chosen from methyl violet, neutral red, para red, amaranth, carmoisine, allura red AC, tartrazine, orange G, ponceau 4R, methyl red, and murexide-ammonium purpurate. In certain such embodiments, said biological stain is chosen from safranin O, basic fuchsin, acid fuschin, 3,3' dihexylocarbocyanine iodide, carminic acid, and indocyanine green. In certain such embodiments, said carotenoid is chosen from crocetin, a-crocin (S,S-diapo-S,S-carotenoic acid), zeaxanthine, lycopene, α-carotene, β-carotene, bixin, and fucoxanthine. In certain such embodiments, said carotenoid is present in the composition as a mixture is selected from the group consisting of saffron red powder, annatto extract, and brown algae extract.

In some embodiments of any of the foregoing or following, the additional chromophore is selected from a group consisting of phloxine B, rose bengal, eosin B, fluorescein, erythrosine B, rhodamine B, rhodamine G, rhodamine WT, saffron red powder, annatto extract, brown algae extract, safranin O, basic fuchsin, acid fuschin, 3,3' dihexylocarbocyanine iodide, carminic acid, indocyanine green, crocetin, α-crocin (8,8-diapo-8,8-carotenoic acid), zeaxanthine, lycopene, α-carotene, β-carotene, bixin, fucoxanthine, methyl violet, neutral red, para red, amaranth, carmoisine, allura red AC, tartrazine, orange G, ponceau 4R, methyl red, murexide-ammonium purpurate, pyronine Y and pyronine B.

In certain embodiments of any of the foregoing or following, the additional chromophore is present in an amount of from about 0.02% to about 12% by weight of the composition, such as from about 0.02% to about 10%, from about 0.02% to about 8%, from about 0.02% to about 6%, from about 0.02% to about 4%, from about 0.02% to about 2%, from about 0.02% to about 1%, or about 5% by weight of the composition.

In some embodiments of any of the foregoing or following, the composition further comprises at least one oxidant. In certain such embodiments, the oxidant is selected from the group consisting of hydrogen peroxide, carbamide peroxide, and benzoyl peroxide. In other embodiments, the oxidant is a peroxy acid or an alkali metal percarbonate.

In some embodiments of any of the foregoing or following, the oxidant is present in an amount of from about 1% to about 70% by weight of the composition, e.g., from about 1% to about 60%, from about 1% to about 50%, from about 1% to about 40%, from about 1% to about 30%, from about 1% to about 20%, from about 1% to about 18%, from about 1% to about 16%, from about 1% to about 14%, from about 1% to about 12%, from about 1% to about 10%, from about 1% to about 8%, from about 1% to about 6%, from about 0.05% to about 6%, from about 0.1% to about 6%, from about 0.5% to about 6%, from about 2.5% to about 6%, from about 3.5% to about 6% by weight of the composition.

In some embodiments of any of the foregoing or following, the oxidant is hydrogen peroxide and is present in an amount of from about 3.5% to about 6% by weight of the composition.

In some embodiments of any of the foregoing or following, the oxidant is carbamide peroxide and is present in an amount of from about 10% to about 16% by weight of the composition.

In some embodiments of any of the foregoing or following, the oxidant is benzoyl peroxide and is present in an amount of from about 2.5% to about 5% by weight of the composition.

In some embodiments of any of the foregoing or following, this disclosure provides a method of inhibiting biofilm formation or disrupting existing or developing biofilm in a subject, comprising topically applying a composition comprising at least one oxidant and at least one chromophore, and illuminating said composition to actinic light to cause photoillumination of the composition. In certain such embodiments, the composition is a biophotonic composition.

In some embodiments of any of the foregoing or following, said composition does not comprise an oxidant, such as an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some embodiments of any of the foregoing or following, the composition further comprises at least one salt selected from the group consisting of one or more bicarbonate salts, one or more carbonate salts, and a combination of the foregoing salts.

In some embodiments of any of the foregoing or following, the at least one bicarbonate salt is selected from the group consisting of ammonium bicarbonate, caesium bicarbonate, potassium bicarbonate, sodium bicarbonate, choline bicarbonate, aminoguanidine bicarbonate, and tetraethylammonium bicarbonate. In certain such embodiments, the bicarbonate salt is sodium bicarbonate or potassium bicarbonate.

In some embodiments of any of the foregoing or following, the at least one carbonate salt is selected from the group consisting of barium carbonate, beryllium carbonate, caesium carbonate, calcium carbonate, cobalt (II) carbonate, copper (II) carbonate, lithium carbonate, magnesium carbonate, nickel (II) carbonate, potassium carbonate, sodium carbonate, and zinc carbonate. In certain such embodiments, the carbonate salt is selected from the group consisting of sodium carbonate, calcium carbonate, and potassium bicarbonate.

In some embodiments of any of the foregoing or following, the disclosure provides a method of inhibiting biofilm formation or disrupting existing or developing biofilm in a subject (e.g., suffering from DFU, VLU, and/or PU), comprising topically applying a composition comprising at least one chromophore; at least one salt, such as a salt selected from the group consisting of one or more bicarbonate salts, one or more carbonate salts, and a combination of the foregoing salts; and a pharmaceutically acceptable carrier; and illuminating said composition to actinic light to cause photoillumination of the composition. In certain such embodiments, the composition is a biophotonic composition.

In some embodiments of any of the foregoing or following, the composition further comprises at least one healing factor, such as hyaluronic acid, glucosamine, or allantoin.

In certain embodiments of any of the foregoing or following, said composition further comprises at least one buffering agent chosen from ethylenediaminetetraacetic acid (EDTA) and ethylene glycol tetraacetic acid (EGTA). In certain embodiments of any of the foregoing or following, the chelating agent is EDTA.

In certain embodiments of any of the foregoing or following, the composition further comprises at least one hydrophilic gelling agent. In certain such embodiments, the hydrophilic gelling agent is selected from the group consisting of glucose, modified starch, methyl cellulose, carboxymethyl cellulose, propyl cellulose, hydroxypropyl cellulose, Carbopol® polymers, alginic acid, sodium alginate, potassium alginate, ammonium alginate, calcium alginate, agar, carrageenan, locust bean gum, pectin, and gelatin. The hydrophilic gelling agent enhances the consistency of the composition and contributes to facilitating the application of the composition to the skin or area of biofilms.

In some embodiments of any of the foregoing or following, said composition is illuminated with actinic light, such as a LED light, for at least one treatment period of from about 1 minute to about 30 minutes per $cm^2$ of an area to be treated. In certain such embodiments, said composition is illuminated with actinic light for at least one treatment period of from about 4 minutes to about 26 minutes, from about 8 minutes to about 24 minutes, from about 10 minutes to about 20 minutes, from about 10 minutes to about 18 minutes; or from about 1 minutes to about 5 minutes, from about 5 minutes to about 10 minutes, from about 10 minutes to about 15 minutes, from about 15 minutes to about 20 minutes, from about 20 minutes to about 25 minutes, or about 5 minutes, about 10 minutes, about 15 minutes, or about 20 minutes per $cm^2$ of an area to be treated, such as an area of biofilms.

In some embodiments of any of the foregoing or following, said composition is illuminated with actinic light for at least one treatment period of from about 1 minute to about 9 minutes per $cm^2$ of an area to be treated. In certain such embodiments, said composition is illuminated with actinic light for at least one treatment period of from about 2 minutes to about 8 minutes, from about 3 minutes to about 7 minutes, from about 4 minutes to about 6 minutes, or from about 5 minutes per $cm^2$ of an area to be treated.

In some embodiments of any of the foregoing or following, said composition is illuminated with actinic light for at least two treatment periods (e.g., two consecutive treatment periods). In certain such embodiments, said composition is illuminated with actinic light for at least two treatment periods, each treatment period followed by a resting interval.

In some embodiments of any of the foregoing or following, the resting interval is from about 1 minute to about 30 minutes, such as from about 4 minutes to about 26 minutes, from about 8 minutes to about 24 minutes, from about 10 minutes to about 20 minutes, from about 10 minutes to about 18 minutes; or from about 1 minutes to about 5 minutes, from about 1 minute to about 2 minutes, from about 1 minute to about 3 minutes, from about 2 minutes to about 8 minutes, from about 3 minutes to about 7 minutes, from about 4 minutes to about 6 minutes, from about 5 minutes to about 10 minutes, from about 5 minutes to about 10 minutes, from about 10 minutes to about 15 minutes, from about 15 minutes to about 20 minutes, from about 20 minutes to about 25 minutes, or about 5 minutes, about 10 minutes, about 15 minutes, or about 20 minutes per $cm^2$ of an area to be treated, such as an area of biofilms.

In some embodiments of any of the foregoing or following, said composition is illuminated with at least two treatment periods (e.g., two consecutive treatment periods) of actinic light wherein each treatment period is from about 1 minute to about 10 minutes per $cm^2$ of an area to be treated (e.g., e.g., from about 2 minutes to about 8 minutes, from about 3 minutes to about 7 minutes, from about 4 minutes to about 6 minutes, or about 5 minutes), wherein each treatment period is followed by a resting interval for from about 1 minute to about 10 minutes (e.g., from about 2 minutes to about 8 minutes, from about 3 minutes to about 7 minutes, from about 4 minutes to about 6 minutes, from about 1 minute to about 2 minutes, from about 1 minute to about 3 minutes, from about 5 minutes to about 10 minutes, or about 5 minutes).

In some embodiments of any of the foregoing or following, said composition is illuminated with at least two treatment periods (e.g., two consecutive treatment periods) of actinic light wherein each treatment period is from about 1 minute to about 5 minutes per $cm^2$ of an area to be treated, wherein each treatment period is followed by a resting interval for from about 1 minute to about 10 minutes (e.g., from about 2 minutes to about 8 minutes, from about 3 minutes to about 7 minutes, from about 4 minutes to about 6 minutes, from about 1 minute to about 2 minutes, from about 1 minute to about 3 minutes, from about 5 minutes to about 10 minutes, or about 5 minutes).

In some embodiments of any of the foregoing or following, said composition is illuminated with at least two treatment periods (e.g., two consecutive treatment periods) of actinic light wherein each treatment period is from about 1 minute to about 5 minutes per $cm^2$ of an area to be treated, wherein each treatment period is followed by a resting interval for from about 5 minutes.

In some embodiments of any of the foregoing or following, said method further comprising:
a) topically applying the composition to the subject's area of biofilm;
b) illuminating the subject's area of biofilm to actinic light for a treatment period of from about 1 minute to about 10 minutes (e.g., from about 1 minute to 5 minutes or about 5 minutes);
c) removing the source of actinic light away from the subject's area of biofilm for a resting interval of from about 1 minute to about 10 minutes (e.g., from about 1 minute to 5 minutes, or about 5 minutes);
d) illuminating the subject's area of biofilm to actinic light for a second treatment period of from about 1 minute to about 10 minutes (e.g., from about 1 minute to 5 minutes, or about 5 minutes); and wherein the first illumination to actinic light activates the composition.

In some embodiments of any of the foregoing or following, said method further comprising:
a) topically applying the composition to the subject's area of biofilm;
b) illuminating the subject's area of biofilm to actinic light for a treatment period of from about 1 minute to about 10 minutes (e.g., from about 1 minute to 5 minutes or about 5 minutes);
c) removing the source of actinic light away from the subject's area of biofilm for a resting interval of from about 1 minute to about 5 minutes;
d) illuminating the subject's area of biofilm to actinic light for a second treatment period of from about 1 minute to about 10 minutes (e.g., from about 1 minute to 5 minutes or about 5 minutes); and wherein the first illumination to actinic light activates the composition.

In some embodiments of any of the foregoing or following, the method further comprises topically re-applying the composition before each treatment period, e.g., before the second treatment period.

In some embodiments of any of the foregoing or following, the source of actinic light is illuminating in continuous motion over an area to be treated.

In some embodiments of any of the foregoing or following, the source of actinic light is positioned over an area to be treated. In some embodiments, said actinic light is visible light having a wavelength between about 400 nm and about 700 nm.

In some embodiments of any of the foregoing or following, the subject is a mammal, such as a human, an equine, a feline, or a canine.

In some embodiments of any of the foregoing or following, the biofilm is associated with the subject's skin. In other embodiments, the biofilm is associated with the subject's soft tissues.

In some embodiments of any of the foregoing or following, the biofilm comprises *Staphylococcus aureus*.

In some embodiments of any of the foregoing or following, the biofilm comprises *Pseudomonas aeruginosa*.

In some embodiments of any of the foregoing or following, the biofilm comprises *Staphylococcus aureus* and *Pseudomonas aeruginosa*.

In some embodiments of any of the foregoing or following, the biofilm comprises gram-negative bacteria. In other embodiments, the biofilm comprises gram-positive bacteria.

In some embodiments of any of the foregoing or following, the biofilm is formed by a microorganism.

In some embodiments of any of the foregoing or following, the biofilm comprises a polysaccharide, protein, or glycopeptide produced by a microorganism.

In some embodiments of any of the foregoing or following, the biofilm is produced by bacteria. In other embodiments, the biofilm is produced by yeast. In other embodiments, the biofilm is produced by fungi.

In some embodiments of any of the foregoing or following, the subject is a mammal, such as a human, an equine, a feline, or a canine.

In some aspects, the disclosure provides for use of a composition for the manufacture of a medicament for inhibiting biofilm formation or disrupting existing or developing biofilms in a subject (e.g., suffering from VLU, DFU, and/or PU), wherein said composition comprises at least one chromophore and a pharmaceutically acceptable carrier. In certain aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

In some aspects, the disclosure provides for use of a composition for inhibiting biofilm formation or disrupting existing or developing biofilms in a subject (e.g., suffering from VLU, DFU, and/or PU), the composition comprising: at least one chromophore and a pharmaceutically acceptable carrier. In certain such aspects, the composition further comprises at least one oxidant. In other aspects, the composition further comprises one or more salts selected from the group consisting of one or more bicarbonate salts, one or more carbonate salts, and a combination of the foregoing salts. In certain aspects, the composition further comprises at least one healing factor, e.g., hyaluronic acid, glucosamine, or allantoin.

Compositions

The present disclosure provides methods and uses comprising a composition, e.g., a composition for inhibiting biofilm formation or disrupting existing or developing biofilms in a subject. In one aspect, the composition of the present disclosure is a biophotonic composition. Compositions of this disclosure, in a broad sense, are activated by light (e.g., photons) of specific wavelength. These compositions contain at least one exogenous chromophore which is capable of absorbing light and accelerates the dispersion of light energy.

When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths ('Stokes' shift'). The emitted fluorescent energy can then be transferred to the other components of the composition or to a treatment site on to which the composition is topically applied. Differing wavelengths of light may have different and complementary therapeutic effects on tissue.

In certain embodiments, the compositions of the present disclosure are substantially transparent/translucent and/or have high light transmittance in order to permit light dissipation into and through the composition.

The % transmittance of the composition can be measured in the range of wavelengths from 250 nm to 800 nm using, for example, a Perkin-Elmer Lambda 9500 series UV-visible spectrophotometer. Alternatively, a Synergy HT spectrophotometer (BioTek Instrument, Inc.) can be used in the range of wavelengths from 380 nm to 900 nm.

Transmittance is calculated according to the following equation:

$$A_\lambda = \log_{10} \frac{I_0}{I} = \log_{10} \frac{1}{T}.$$

where A is absorbance, T is transmittance, $I_0$ is intensity of radiation before passing through material, and I is intensity of light passing through material.

The values can be normalized for thickness. As stated herein, % transmittance (translucency) is as measured for a 2 mm thick sample at a wavelength of 526 nm. It will be clear that other wavelengths can be used.

In certain embodiments of the disclosure, the compositions of the present disclosure are for topical uses. The composition can be in the form of a semi-solid or viscous liquid, such as a gel, or are gel-like, and which have a spreadable consistency at room temperature (e.g., about 20-25° C.) prior to illumination. In certain such embodiments wherein the composition has a spreadable consistency, the composition can be topically applied to a treatment site at a thickness of from about 0.5 mm to about 3 mm, from about 0.5 mm to about 2.5 mm, or from about 1 mm to about 2 mm. In some embodiments, the composition can be topically applied to a treatment site at a thickness of about 2 mm or about 1 mm. Spreadable compositions can conform to a topography of a treatment site. This can have advantages over a non-conforming material in that a better and/or more complete illumination of the treatment site can be achieved and the compositions are easy to apply and remove.

These compositions may be described based on the components making up the composition. Additionally or alternatively, the compositions of the present disclosure have functional and structural properties and these properties may also be used to define and describe the compositions. Individual components of the composition of the present disclosure are detailed as below.

Oxidants

In certain embodiments, the composition of the present disclosure may contain an oxidant. In certain embodiments, the oxidant is a peroxide compound; peroxide compounds are oxidants that contain the peroxy group (R—O—O—R), which is a chainlike structure containing two oxygen atoms, each of which is bonded to the other and a radical or some element. Suitable oxidants for preparation of the active medium include, but are not limited to:

Hydrogen peroxide ($H_2O_2$) is the starting material to prepare organic peroxides. $H_2O_2$ is a powerful oxidizing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is less than about 12%, or from about 1% to about 12%, preferably from about 3.5% to about 12% and most preferably from about 3.5% to about 6%.

Urea hydrogen peroxide (also known as urea peroxide, carbamide peroxide or percarbamide) is soluble in water and contains approximately 36% hydrogen peroxide. Carbamide peroxide for use in this composition can be used as a gel, for example with 16% carbamide peroxide that represents approximately 5.6% hydrogen peroxide. A suitable range of concentration over which urea peroxide can be used in the present composition is less than 36%, or from about 3% to about 36%, and preferably from about 10% to about 36% and most preferably from about 3% to about 16%. Urea peroxide breaks down to urea and hydrogen peroxide in a slow-release fashion that can be accelerated with heat or photochemical reactions. The released urea [carbamide, $(NH_2)CO_2)$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acid. Benzoyl peroxide breaks down to benzoic acid and oxygen upon contact with skin, neither of which are toxic. A suitable range of concentration over which benzoyl peroxide can be used in the present composition is less than about 10%, or from about 1% to about 10%, or preferably from about 1% to about 8%, and most preferably from about 2.5% to about 5%.

Suitable oxidants may also include peroxy acids and alkali metal percarbonates, but the inclusion of any other forms of peroxides (e.g. organic or inorganic peroxides) should be avoided due to their increased toxicity and their unpredictable reaction with the photodynamic energy transfer.

Chromophores

The compositions, such as biophotonic topical compositions, the methods and uses of the present disclosure comprise one or more chromophores, which can be considered exogenous, e.g., are not naturally present in skin or tissue. When a composition of the present disclosure is illuminated with light, the chromophore(s) are excited to a higher energy state. When the chromophore(s)' electrons return to a lower energy state, they emit photons with a lower energy level, thus causing the emission of light of a longer wavelength (Stokes' shift).

Suitable chromophores for the compositions of the disclosure can be fluorescent dyes (or stains), although other dye groups or dyes (biological and histological dyes, food colorings, carotenoids, naturally occurring fluorescent and other dyes) can also be used.

In some embodiments, the composition of the present disclosure comprises a chromophore which undergoes partial or complete photobleaching upon application of light. By photobleaching is meant a photochemical destruction of the chromophore which can generally be visualized as a loss of color.

In some embodiments, the chromophore absorbs at a wavelength in the range of the visible spectrum, such as at a wavelength of from about 380-800 nm, about 380-700 nm, or about 380-600 nm. In some embodiments, the chromophore absorbs at a wavelength of about 200-800 nm, about 200-700 nm, about 200-600 nm or about 200-500 nm. In some embodiments, the chromophore absorbs at a wavelength of about 200-600 nm. In some embodiments, the chromophore absorbs light at a wavelength of about 200-300 nm, about 250-350 nm, about 300-400 nm, about 350-450 nm, about 400-500 nm, about 400-600 nm, about 450-650 nm, about 600-700 nm, about 650-750 nm or about 700-800 nm.

In some embodiments, the chromophore or combination of chromophores is present in an amount of about 0.001-40% by weight of the composition. In some embodiments, the chromophore or combination of chromophores is present in an amount of about 0.005-2%, about 0.01-1%, about 0.01-2%, about 0.05-1%, about 0.05-2%, about 0.1-1%, about 0.1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the chromophore or combination of chromophores is present in an amount of at least about 0.2% by weight of the composition.

In some embodiments, the chromophore or combination of chromophores is present in an amount of from 0.001-40% by weight of the composition. In some embodiments, the chromophore or combination of chromophores is present in an amount of 0.005-2%, 0.01-1%, 0.01-2%, 0.05-1%, 0.05-2%, 0.1-1%, 0.1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the chromophore or combination of chromophores is present in an amount of at least 0.2% by weight of the composition.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectra) measured in a composition of the present disclosure.

The compositions disclosed herein may include at least one additional chromophore. Combining chromophores may increase photo-absorption by the combined dye molecules and enhance absorption and photo-biomodulation selectivity. This creates multiple possibilities of generating new photosensitive, and/or selective chromophores mixtures.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur the emission spectrum of the donor chromophore overlap with the absorption spectrum of the acceptor chromophore.

Energy transfer manifests itself through decrease or quenching of the donor emission and a reduction of excited state lifetime accompanied also by an increase in acceptor emission intensity.

To enhance the energy transfer efficiency, the donor chromophore should have good abilities to absorb photons and emit photons. Furthermore, it is thought that the more overlap there is between the donor chromophore's emission spectra and the acceptor chromophore's absorption spectra, the better a donor chromophore can transfer energy to the acceptor chromophore.

In some embodiments, the biophotonic topical composition of the present disclosure further comprises an acceptor, or a second, chromophore. In some embodiments, the donor, or first, chromophore has an emission spectrum that overlaps at least about 80%, about 70%, about 60%, about 50%, about 40%, about 30%, about 20%, or about 10% with an absorption spectrum of the second chromophore. In some embodiments, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

% spectral overlap, as used herein, refers to the % overlap of a donor chromophore's emission wavelength range with an acceptor chromophore's absorption wavelength range, measured at spectral full width quarter maximum (FWQM). The spectral FWQM of the acceptor chromophore's absorption spectrum is from about 60 nm (about 515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum, e.g., 400-700 nm. In some embodiments, the second chromophore has an absorption wavelength that is relatively longer than that of the first chromophore within the range of about 50-250 nm, about 25-150 nm or about 10-100 nm.

As discussed above, the application of light to the compositions of the present disclosure can result in a cascade of energy transfer between the chromophores. In some embodiments, such a cascade of energy transfer provides photons that penetrate the epidermis, dermis and/or mucosa at the target tissue, including, such as, a site of wound.

In some embodiments, the chromophore or chromophores are selected such that their emitted fluorescent light, on photoillumination, is within one or more of the green, yellow, orange, red and infrared portions of the electromagnetic spectrum, for example having a peak wavelength within the range of about 490 nm to about 800 nm. In some embodiments, the emitted fluorescent light has a power density of between 0.005 to about 10 mW/cm$^2$, about 0.5 to about 5 mW/cm$^2$.

Suitable chromophores useful in the compositions (such as the biophotonic compositions), methods, and uses of the present disclosure include, but are not limited to the following:

Xanthene Derivatives

The xanthene derivative dyes have been used and tested for a long time worldwide. They display low toxicity and increased fluorescence. The xanthene group consists of 3 sub-groups that are: a) the fluorenes; b) fluorones; and c) the rhodoles.

The fluorenes group comprises the pyronines (e.g. pyronin Y and B) and the rhodamines (e.g. rhodamine B, G and WT). Depending on the concentration used, both pyronines and rhodamines may be toxic and their interaction with light may lead to increased toxicity. Similar effects are known to occur for the rhodole dye group.

The fluorone group comprises the fluorescein dye and the fluorescein derivatives.

Fluorescein is a fluorophore commonly used in microscopy with an absorption max. of 494 nm and an emission max. of 521 nm. The disodium salt of fluorescein is known as D&C Yellow 8. It has very high fluorescence but photodegrades quickly. In the present composition, mixtures of fluorescein with other chromophores such as indocyanin green and/or saffron red powder will confer increased photoadsorption to these other compounds.

Eosins group comprises eosin Y (tetrabromofluorescein, acid red 87, D&C Red 22) with an abs. max 514-518 nm, stains cytoplasm of cells, collagen, muscle fibers and red blood cells intensely red; and eosin B (acid red 91, eosin scarlet, dibromo-dinitrofluorescein), with the same staining characteristics as eosin Y. Eosin Y and eosin B are collectively referred to as "Eosin", and use of the term "Eosin" refers to either eosin Y, eosin B or a mixture of both. Eosin Y, eosin B, or a mixture of both can be used because of their sensitivity to the light spectra used: broad spectrum blue light, blue to green light and green light. Their tissue and biofilm staining properties and their low toxicity are also advantageous. Both eosin Y and eosin B stain red blood cells and thus confer to the composition of the present disclosure haemostatic (controls the flow or stops the flow of blood) properties as well as increase the selective targeting of light to the soft tissues of the lesion or wound during the application of the composition. In embodiments, the composition includes in the range of less than about 12% of at least one of eosin B or eosin Y or combinations thereof, or from about 0.02% to about 12% of at least one of eosin B or eosin Y or combinations thereof, or between about 0.02% and about 1.2%, or from about 0.02% to about 0.5%, or from about 0.5% to about 0.8% of at least one of eosin B or eosin Y or combinations thereof. In yet another embodiment, the composition includes less than 12% of at least one of eosin B or eosin Y or combinations thereof, or from about 0.02% to about 12% of at least one of eosin B or eosin Y or combinations thereof, or between about 0.02% and about 1.2%, or from about 0.02% to about 0.5%, or from about 0.02% to about less than 0.5% or from about 0.5% to about 0.8% of at least one of eosin B or eosin Y or combinations thereof, and/or less than about 2% erythrosine B, or from about 0.005 to about 2% erythrosine B, or from about 0.005% to about 1%, or about 0.01% to about 1%, or about 0.005% and about 0.15% of erythrosine B.

Phloxine B (2,4,5,7-tetrabromo 4,5,6,7,tetrachlorofluorescein, D&C Red 28, acid red 92) is a red dye derivative of fluorescein which is used for disinfection and detoxification of waste water through photooxidation. It has an abs. max. of 535-548 nm. It is also used as an intermediate for making photosensitive dyes and drugs.

Erythrosine B, or simply Erythrosine (acid red 51, tetraiodofluorescein) is a cherry-pink, coal-based fluorine food dye used as a biological stain, and a biofilm and dental plaque disclosing agent, with max. abs. 524-530 nm in aqueous solution. It is subject to photodegradation. Erythrosine is also used in some embodiments due to its photosensitivity to the light spectra used and its ability to stain biofilms. In embodiments, the composition includes in the range of less than about 2% erythrosine B, or from about 0.005 to about 2% erythrosine B, or from about 0.005% to about 1%, or about 0.01% to about 1%, or about 0.005% and about 0.15% of erythrosine B.

Rose Bengal (4,5,6,7 tetrachloro 2,4,5,7 tetraiodofluorescein, acid red 94) is a bright bluish-pink biological dye with an absorption max. of 544-549 nm, that has been used as a dye, biological stain and diagnostic aid. Also it is used in synthetic chemistry to generate singlet from triplet oxygen.

Merbromine (mercurochrome) is an organo-mercuric disodium salt of fluorescein with an abs. max. of 508 nm. It is used as an antiseptic.

Azo Dyes

The azo (or diazo-) dyes share the N—N group, called azo the group. They are used mainly in analytical chemistry or as food colorings and are not fluorescent. Suitable azo dyes include: Methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), murexide-ammonium purpurate.

Biological Stains

Dye molecules commonly used in staining protocols for biological materials can also be used as chromophores. Suitable biological stains include:

Saffranin (Saffranin 0, basic red 2) is also an azo-dye and is used in histology and cytology. It is a classic counter stain in a Gram stain protocol.

Fuchsin (basic or acid) (rosaniline hydrochloride) is a magenta biological dye that can stain bacteria and has been used as an antiseptic. It has an abs. max. 540-555 nm.

3,3' dihexylocarbocyanine iodide (DiOC6) is a fluorescent dye used for staining cell's endoplasmic reticulum, vesicle membranes and mitochondria. It shows photodynamic toxicity; when illuminated with blue light, has a green fluorescence.

Carminic acid (acid red 4, natural red 4) is a red glucosidal hydroxyanthrapurin naturally obtained from cochineal insects.

Indocyanin green (ICG) is used as a diagnostic aid for blood volume determination, cardiac output, or hepatic function. ICG binds strongly to red blood cells and when used in mixture with fluorescein, it increases the absorption of blue to green light.

Carotenoids

Carotenoid dyes can also act as chromophores.

Saffron red powder is a natural carotenoid-containing compound. Saffron is a spice derived from *Crocus sativus*. It is characterized by a bitter taste and iodoform or hay-like fragrance; these are caused by the compounds picrocrocin and saffranal. It also contains the carotenoid dye crocin that gives its characteristic yellow-red color.

Saffron contains more than 150 different compounds many of them are carotenoids: mangicrocin, reaxanthine, lycopene, and various α and β-carotenes, which show good absorption of light and beneficial biological activity. Also saffron can act as both a photon-transfer agent and a healing factor. Saffron color is primarily the result of α-crocin (8,8 diapo-8,8-carotenoid acid). Dry saffron red powder is highly sensitive to fluctuating pH levels and rapidly breaks down chemically in the presence of light and oxidizing agents. It is more resistant to heat. Data show that saffron has anti-carcinogenic, immunomodulating and antioxidant properties. For absorbance, it is determined for the crocin specific photon wavelength of 440 nm (blue light). It has a deep red colour and forms crystals with a melting point of 186° C. When dissolved in water it forms an orange solution.

Crocetin is another compound of saffron that was found to express an antilipidemic action and promote oxygen penetration in different tissues. More specifically it was observed an increased oxygenation of the endothelial cells of the capillaries. An increase of the oxygenation of muscles and cerebral cortex was observed and led to an increased survival rate in laboratory animals with induced hemorrhagic shock or emphysema.

Anatto is a spice that contains as its main constituent (70-80%) the carotenoid bixin which displayed relevant antioxidative properties.

β-carotene, also displayed suitable characteristics.

Fucoxanthine is a constituent of brown algae with a pronounced ability for photosensitization of red-ox reactions.

Healing Factors

Healing factors comprise compounds that promote or enhance the healing or regenerative process of the tissues on the application site of the composition. During the photoillumination of the composition, there is an increase of the absorption of molecules at the treatment site by the mucosa. An augmentation in the blood flow at the site of treatment is observed for an extent period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Current studies evidenced hyaluronic acid appearing in the early stages of healing to physically create room for white blood cells that mediate the immune response. It is used in the synthesis of biological scaffolds for wound healing applications and in wrinkle treatment. In embodiment, the composition includes in the range of less than about 2% hyaluconic acid, or from about 0.001% to about 2%, or preferable from about 0.002% to about 2%, or from about 0.002% to about 1% hyaluronic acid.

Glucosamine: is one of the most abundant monosaccharides in human tissues and a precursor in the biological synthesis of glycosilated proteins and lipids. It is commonly used in the treatment of osteoarthritis. The common form of glucosamine used is its sulfate salt. Glucosamine shows a number of effects including an anti-inflammatory activity, stimulation of the synthesis of proteoglycans and the synthesis of proteolytic enzymes. A suitable range of concentration over which glucosamine can be used in the present composition is from less than about 5%, or from about 0.0001% to about 5%, or from about 0.0001% to about 3%, and preferable from about 0.001% to about 3%, or from about 0.011% to about 1% and about 1% to about 3%.

Allantoin: is a diureide of glyosilic acid. It has keratolytic effect, increases the water content of the extracellular matrix, enhances the desquamation of the upper layers of dead (apoptotic) skin cells, and promotes skin proliferation and wound healing. In embodiment, the composition includes in the range of less than about 1% allantoin, or from about 0.001% to about 1%, or from about 0.002% to about 1%, or preferably from about 0.02% to about 1%, and most preferably from about 0.02% to about 0.5%.

Also, saffron can act as both a photon-transfer agent and a healing factor.

Buffering Agents

Buffering agents can be included to promote smear layer removal in closed pockets and difficult to reach lesions. In certain embodiments, compounds of the present disclosure comprise buffering agents that act as a metal ion quencher and as a buffer. Suitable chelating agents for the compositions, methods and uses of the disclosure include, but are not limited to:

Ethylenediaminotetraacetic Acid (EDTA)

Ethylenediaminotetraacetic acid (EDTA) is an amino acid and is used to sequester di- and trivalent metal ions. EDTA binds to metals via four carboxylate and two amine groups. EDTA forms especially strong complexes with Mn(III), Fe(III), Cu(III), Co(III). It is used to buffer solutions.

Ethylene Glycol Tetraacetic Acid (EGTA)

Ethylene glycol tetraacetic acid (EGTA) is related to EDTA, but with a much higher affinity for calcium than magnesium ions. It is useful for making buffer solutions that resemble the environment inside living cells.

Carbonate and Bicarbonate Salts

According to some embodiments, the compositions of the present disclosure may optionally further comprise one or more carbonate or bicarbonate salts.

Suitable carbonate or bicarbonate salts that may be present in the composition include, but are not limited to: ammonium bicarbonate, caesium bicarbonate, potassium bicarbonate, sodium bicarbonate, choline bicarbonate, aminoguanidine bicarbonate, tetraethylammonium bicarbonate, barium carbonate, beryllium carbonate, caesium carbonate, calcium carbonate, cobalt (II) carbonate, copper (II) carbonate, lithium carbonate, magnesium carbonate, nickel (II) carbonate, potassium carbonate, sodium carbonate, or zinc carbonate.

In some embodiments, the composition of the disclosure comprises one or more salts selected from bicarbonate salts, carbonate salts or a combination of the foregoing salts. In some embodiments, the composition of the disclosure comprises one or more bicarbonate salts. In some embodiments when the composition comprises one or more bicarbonate salts, the bicarbonate salt is sodium bicarbonate. In some embodiments when the composition comprises one or more bicarbonate salts, the bicarbonate salt is potassium bicarbonate. In some embodiments, the composition of the disclosure comprises one or more carbonate salts. In some embodiments when the composition comprises one or more carbonate salts, the carbonate salt is sodium carbonate. In some embodiments when the composition comprises one or more carbonate salts, the carbonate salt is potassium carbonate. In some embodiments when the composition comprises one or more carbonate salts, the carbonate salt is calcium carbonate.

Gelling Agents

Gelling agents for the compositions, uses or methods according to the present disclosure may comprise any ingredient suitable for use in composition as described herein. The gelling agent may be an agent capable of forming a cross-linked matrix, including physical and/or chemical cross-links. The gelling agent can be biocompatible, and may be biodegradable. In some embodiments, the gelling agent is able to form a hydrogel or a hydrocolloid. An appropriate gelling agent is one that can form a viscous liquid or a semisolid. In some embodiments, the gelling agent and/or the composition has an appropriate light transmission properties. It is also important to select a gelling agent which will allow biophotonic activity of the chromophore(s). For example, some chromophores require a hydrated environment in order to fluoresce. The gelling agent may be able to form a gel by itself or in combination with other ingredients such as water or another gelling agent, or when applied to a treatment site, or when illuminated with light.

The gelling agent according to various embodiments of the present disclosure may include, but not be limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); silicones, polyvinyl silicates, tetramethoxyorthosilicates, methyltrimethoxyorthosilicates, tetraalkoxyorthosilicates, trialkoxyorthosilicates, pressure sensitive silicone adhesives (such as BioPSA from Dow-Corning), and polyvinylamines.

The gelling agent according to some embodiments of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or about 100,000, or about 1,000,000) and/or cross-linked polyacrylic acid polymer.

In some embodiments, the gelling agent comprises a carbomer. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has a pH of approximately 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol®. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994), incorporated herein by reference) and Durrani (Pharmaceutical Res. (Supp.) 8:S-135 (1991), incorporated herein by reference), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In some embodiments, the carbomer is Carbopol® 980 NF, ETD 2020 NF, Ultrez 10 NF, Ultrez 21 or 1382 Polymer, 1342 NF, 940 NF. In some embodiments, about 0.05% to about 10%, about 0.5% to about 5%, or about 1% to about 3% by weight of the final composition of a high molecular weight carbopol can be present as the gelling agent. In some embodiments, the composition of the disclosure comprises about 0.05% to about 10%, about 0.5% to about 5%, or about 1% to about 3% by weight of the final composition of a high molecular weight carbopol.

In some embodiments, the gelling agent comprises a hygroscopic and/or a hydrophilic material useful for their water attracting properties. The hygroscopic or hydrophilic material may include, but is not limited to, glucosamine, glucosamine sulfate, polysaccharides, cellulose derivatives (hydroxypropyl methylcellulose, hydroxyethyl cellulose, hydroxypropyl cellulose, methylcellulose and the like), non-cellulose polysaccharides (galactomannans, guar gum, carob gum, gum arabic, sterculia gum, agar, alginates and the like), glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate). In some embodiments, the hydrophilic gelling agent is selected from glucose, modified starch, methyl cellulose, carboxymethyl cellulose, propyl cellulose, hydroxypropyl cellulose, carbomers, alginic acid, sodium alginate, potassium alginate, ammonium alginate, calcium alginate, agar, carrageenan, locust bean gum, pectin, and gelatin.

The gelling agent may be protein-based/naturally derived material such as sodium hyaluronate, gelatin or collagen, lipids, or the like. The gelling agent may be a polysaccharide such as starch, chitosan, chitin, agarose, agar, locust bean gum, carrageenan, gellan gum, pectin, alginate, xanthan, guar gum, and the like.

In some embodiments, the composition can include up to about 2% by weight of the final composition of sodium hyaluronate as the single gelling agent. In some embodiments, the composition can include more than about 4% or more than about 5% by weight of the final composition of gelatin as the single gelling agent. In some embodiments, the composition can include up to about 10% or up to about 8% starch as the single gelling agent. In some embodiments, the composition can include more than about 5% or more than about 10% by weight of the final composition of collagen as the gelling agent. In some embodiments, about 0.1% to about 10% or about 0.5% to about 3% by weight of the final composition of chitin can be used as the gelling agent. In some embodiments, from about 0.5% to about 5% by weight of the final composition of corn starch or from about 5% to about 10% by weight of the final composition of corn starch can be used as the gelling agent. In some embodiments, more than about 2.5 wt % by weight of the final composition of alginate can be used in the composition as the gelling agent. In some embodiments, the percentages by weight percent of the final composition of the gelling agents can be as follows: cellulose gel (from about 0.3% to about 2.0%), konjac gum (from about 0.5% to about 0.7%), carrageenan gum (from about 0.02% to about 2.0%), xanthan gum (from about 0.01% to about 2.0%), acacia gum (from about 3% to about 30%), agar (from about 0.04% to about 1.2%), guar gum (from about 0.1% to about 1%), locust bean gum (from about 0.15% to about 0.75%), pectin (from about 0.1% to about 0.6%), tara gum (from about 0.1% to about 1.0%), polyvinylypyrrolidone (from about 1% to about 5%), sodium polyacrylate (from about 1% to about 10%). Other gelling agents can be used in amounts sufficient to gel the composition or to sufficiently thicken the composition. It will be appreciated that lower amounts of the above gelling agents may be used in the presence of another gelling agent or a thickener.

The composition of the present disclosure may be further encapsulated, e.g., in a membrane. Such a membrane may be transparent, and/or substantially, or fully impermeable. The membrane may be impermeable to liquid but permeable to gases such as air. In some embodiments, the composition may form a membrane that encapsulates the chromophore(s) of the biophotonic topical composition, where the membrane may be substantially impermeable to liquid and/or gas. The membrane may be formed of one or more lipidic agents, polymers, gelatin, cellulose or cyclodextrins, or the like. In some embodiments, the membrane is translucent or transparent to allow light to infiltrate to and from the chromophore(s). In some embodiments, the composition is a dendrimer with an outer membrane comprising poly (propylene amine). In some embodiments, the outer membrane comprises gelatin.

Polyols

According to some embodiments, the compositions of the methods and uses of the present disclosure may optionally further comprise one or more polyols. Suitable polyols that may be included in the composition include, but are not limited to a diol, a triol, a saccharide, glycerine, butane-1, 2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol. In some embodiments when the composition of the disclosure includes one or more polyols, the polyol is glycerine. In some embodiments when the composition of the disclosure includes one or more polyols, the polyol is propylene glycol. In some embodiments when the composition of the disclosure includes one or more polyols, the polyol is a combination of glycerine and propylene glycol.

In some embodiments, one or more polyols are present in an amount of about 5-75% by weight of the total composition, such as 5-75% by weight of the total composition. In some embodiments, one or more polyols are present in an amount of about 10-75% by weight of the total composition, such as 10-75% by weight of the total composition. In some embodiments, one or more polyols are present in an amount of about 15-75% by weight of the total composition, such as 15-75% by weight of the total composition. In some embodiments, one or more polyols are present in an amount of about 20-75% by weight of the total composition, such as 20-75% by weight of the total composition.

Additional Components

The compositions, methods, and uses of the disclosure can also include other ingredients such as humectants (e.g., glycerine, ethylene glycol, and propylene glycol), preservatives such as parabens, and pH adjusters such as sodium hydroxide, sodium bicarbonate, and HCl. In some embodiments, the pH of the composition is in or adjusted to the range of about 4 to about 10. In some embodiments, the pH of the composition is in or adjusted to the range of about 4 to about 9. In some embodiments, the pH of the composition is in or adjusted to the range of about 4 to about 8. In some embodiments, the pH of the composition is within the range of about 4 to about 7. In some embodiments, the pH of the composition is within the range of about 4 to about 6.5. In some embodiments, the pH of the composition is within the range of about 4 to about 6. In some embodiments, the pH of the composition is within the range of about 4 to about 5.5. In some embodiments, the pH of the composition is within the range of about 4 to about 5. In some embodiments, the pH of the composition is within the range of about 5.0 to about 8.0. In some embodiments, the pH of the composition is within the range of about 6.0 to about 8.0. In some embodiments, the pH of the composition is within the range of about 6.5 to about 7.5. In some embodiments, the pH of the composition is within the range of about 5.5 to about 7.5.

In some embodiments, the pH of the composition is in or adjusted to the range of 4 to 10. In some embodiments, the pH of the composition is in or adjusted to the range of 4 to 9. In some embodiments, the pH of the composition is in or adjusted to the range of 4 to 8. In some embodiments, the pH of the composition is within the range of 4 to 7. In some embodiments, the pH of the composition is within the range of 4 to 6.5. In some embodiments, the pH of the composition is within the range of 4 to 6. In some embodiments, the pH of the composition is within the range of 4 to 5.5. In some embodiments, the pH of the composition is within the range of 4 to 5. In some embodiments, the pH of the composition is within the range of 5.0 to 8.0. In some embodiments, the pH of the composition is within the range of 6.0 to 8.0. In some embodiments, the pH of the composition is within the range of 6.5 to 7.5. In some embodiments, the pH of the composition is within the range of 5.5 to 7.5.

In some embodiments, the compositions of the disclosure also include an aqueous substance (water) or an alcohol. Alcohols include, but are not limited to, ethanol, propanol, isopropanol, butanol, iso-butanol, t-butanol or pentanol. In some embodiments, the chromophore or combination of chromophores is in solution in a medium of the composition. In some embodiments, the chromophore or combination of chromophores is in solution in a medium of the composition, wherein the medium is an aqueous substance.

Methods of Use and Treatment

As discussed above, biofilms are mucilaginous communities of microorganisms such as bacteria, archaea, fungi, molds, algae or protozoa or mixtures thereof that grow on various surfaces. Biofilms form when microorganisms establish themselves on a surface and activate genes involved in producing a matrix that includes polysaccharides. This matrix may provide protection of biofilm forming bacteria from biocides.

Microbial cells can grow as a single-cell free living organism (planktonic) or as cell aggregates in the form of biofilms. Biofilms are physiologically distinct from planktonic cells of the same organism, which, by contrast, are single-cells that may float or swim in a liquid medium. Biofilms are composed of highly organized communities of microorganisms which are surrounded by an extracellular matrix (ECM). The ECM is typically a microbial-derived complex comprising polysaccharides, proteins, lipids, and nucleic acids. Additionally, the ECM may contain host-derived components such as fibrin, platelets, and immunoglobulins (see, Harper, D. R. et. al; "Bacteriophages and Biofilms", Antibiotics, 2015, 3, 270-284; doi:10.3390/antibiotics3030270)

Biofilms can be formed by different microorganism species and genera including bacteria, archaea, fungi, molds, algae or protozoa or mixtures thereof that grow on various surfaces. Bacteria involved in the formation of biofilms include both gram negative and gram positive bacteria. Gram-negative bacteria are a group of bacteria which do not absorb crystal violet during the Gram stain test and include bacteria such as *Pseudomona aeruginosa* (*P. aeruginosa*), *Escherichia coli* (*E. coli*), *Neisseria gonorrhoeae*, *Chlamydia trachomatis*, *Proteus mirabilis*, and *Yersinia pestis*. Gram-positive bacteria are a group of bacteria which absorb crystal violet during the Gram stain test. The Gram-positive bacteria typically have thick peptidoglycan layer in the bacterial cell wall retains the stain. Some exemplary examples of Gram-positive bacteria include *Staphylococcus aureus* (*S. aureus*), *Bacillus* spp, *Listeria monocytogenes*, *Staphylococcus* spp, and lactic acid bacteria, including *Lactobacillus plantarum* and *Lactococcus lactis*.

Biofilm-related infections can be divided into two major groups: device-related or tissue-related. Device-related biofilms are involved in many hospital-acquired infections in which they are known to contaminate devices such as implants and catheters and to prevent adequate antimicrobial treatment of such devices. Tissue-related biofilms often result in adverse health conditions following their involvement in diseases such as chronic obstructive pulmonary disease, tuberculosis, chronic wound infections, chronic otitis media, chronic sinusitis, lung infections such as cystic fibrosis, and tooth decay.

The duration of the exposure to actinic light will be dependent on the surface of the treated area, and on the type of lesion, trauma or injury that is being treated. The illumination of the composition may take place within seconds or even fragment of seconds, but a prolonged exposure period is beneficial to exploit the synergistic effects of the absorbed, reflected and reemitted light on the composition of the present disclosure and its penetration in the tissue being treated. In some embodiments, the time of exposure to actinic light of the tissue on which the composition has been applied is a period of less than 5 minutes. In other embodiments, the time of exposure is from about 20 seconds to about 5 minutes, or from between about 60 second and about 5 minutes. In other embodiments, the time of exposure to actinic light of the tissue on which the composition has been applied is a period of less than about 5 minutes. In other embodiments, the time of exposure is between about 20 seconds to about 5 minutes, or between about 60 seconds and about 5 minutes per $cm^2$ of the area to be treated, so that the total time of exposure of a 10 $cm^2$ area would be between 10 minutes and 50 minutes. In yet other embodiments, the source of actinic light is in continuous motion over the treated area for the appropriate time of exposure. In yet other embodiments, multiple applications of the composition and actinic light are performed. In some embodiments, the tissue, skin or wound is exposed to actinic light at least two, three, four, five or six times, or more, depending on the patient's requirement. Also, the entire treatment may be repeated in its entirety as may be required by the patient. In some embodiments, a fresh application of the composition is applied before exposure to actinic light.

Combination Treatments

In some embodiments, compositions of the present disclosure may be used with other therapeutic treatments. The phrase "combination therapy" embraces the application of any of the compositions described herein, and an additional therapeutic regime, or combination of them, as part of a specific treatment regimen intended to provide a beneficial effect from the co-action of these therapeutic regime. Application of these therapeutic regimes in combination typically is carried out over a defined time period (usually minutes, hours, days or weeks depending upon the combination selected). Typically, "combination therapy" is intended to embrace application of these therapeutic regimes in a sequential manner, that is, wherein each regimen is applied at a different time, as well as, or alternatively application of these regimes, or at least two of the compositions, in a substantially simultaneous manner. The therapeutic agents can be applied by the same route or by different routes. Alternatively, for example, all therapeutic agents may be applied topically. "Combination therapy" also can embrace the application of the compositions as described herein in further combination with other biologically active ingredients (such as, but not limited to, a second and different therapeutic agent) and non-drug therapies (such as, but not limited to, surgery or radiation).

In some embodiments, the therapeutic agents utilized in a combination therapy may be utilized simultaneously, separately, or sequentially with any of the compounds and compositions of this disclosure, or mixtures thereof, and may comprise, but are not limited to: a non-steroidal anti-inflammatory drug (NSAID), an anti-inflammatory agent, a corticosteroid, an anti-allergic agent, a steroid drug, one or more of the antimicrobial agents described above, one or more collagens and/or agents that promote collagen synthesis described above, or mixtures thereof.

In some embodiments, any of the compositions described herein can allow the combination therapeutic agents and/or compositions described herein or mixtures thereof to be utilized at a low dose, that is, at a dose lower than has been conventionally used in clinical situations.

Alternatively, the methods and combinations of this disclosure may allow for maximizing a therapeutic effect at higher doses.

In some embodiments, when utilized as a combination, the therapeutic agents can be formulated as separate compositions which are given at the same time or different times, or the therapeutic agents can be given as a single composition.

Kits

The present disclosure also provides kits for preparing and/or applying any of the compositions of the present disclosure for inhibiting biofilm formation or disrupting existing or developing biofilms in a subject. The kit may include a composition as described above (e.g., a biophotonic topical composition), and may also include a light source, an apparatus for applying or removing the composition, and instructions of use for the composition and/or a light source. In some embodiments, the composition comprises at least one oxidant and at least one chromophore capable of activating the oxidant. In other embodiments, the composition comprises at least one chromophore and at least one salt selected from bicarbonate salts, carbonate salts, or a combination of foregoing salts.

In some embodiments, the kit includes more than one composition, for example, a first and a second composition. The first composition may include at least one chromophore and the second composition may include at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the kit includes more than one composition, for example, a first and a second composition. The first composition may include at least one chromophore and the second composition may include at least one salt selected from bicarbonate salts, carbonate salts, or a combination of foregoing salts. In certain such embodiments, the first and/or second composition further comprises one or more gelling agents.

In some embodiments, the first composition may comprise the at least one chromophore in a liquid or as a powder, and the second composition may comprise at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the first composition may comprise the at least one chromophore, and the second composition may comprise at least one salt selected from bicarbonate salts, carbonate salts, or a combination of foregoing salts. In certain such embodiments, the first and/or second composition further comprises one or more gelling agents.

In some embodiments, the kit includes containers comprising the compositions of the present disclosure. In some embodiments, the kit includes a first container comprising the at least one chromophore and a second container comprising at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the kit includes containers comprising the compositions of the present disclosure. In some embodiments, the kit includes a first container comprising the at least one chromophore and a second container comprising at least one salt selected from bicarbonate salts, carbonate salts, or a combination of foregoing salts. In certain such embodiments, the first and/or second composition further comprises one or more gelling agents.

The containers may be light impermeable, air-tight and/or leak resistant. Exemplary containers include, but are not limited to, syringes, vials, or pouches. The first and second compositions may be included within the same container but separated from one another until a user mixes the compositions. In some embodiments, the container may be a dual-chamber syringe where the contents of the chambers mix on expulsion of the compositions from the chambers. In some embodiments, the pouch may include two chambers separated by a frangible membrane. In some embodiments, one component may be contained in a syringe and injectable into a container comprising the second component.

The composition may also be provided in a container comprising one or more chambers for holding one or more components of the composition, and an outlet in communication with the one or more chambers for discharging the composition from the container.

In some embodiments, the kit comprises a systemic or topical drug for augmenting the treatment of the composition. For example, in certain such embodiments, the kit may include a systemic or topical agent, e.g., an anesthetics or anti-inflammation agent, for reducing pain.

Written instructions on how to use the composition in accordance with the present disclosure may be included in the kit, or may be included on or associated with the containers comprising the compositions of the present disclosure.

In some embodiments, the kit may comprise a further component which is a dressing. The dressing may be a porous or semi-porous structure for receiving the composition. The dressing may comprise woven or non-woven fibrous materials.

In some embodiments of the kit, the kit may further comprise a light source such as a portable light with a wavelength appropriate to activate the chromophore in the composition. The portable light may be battery operated or re-chargeable.

In some embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

It should be appreciated that the disclosure is not limited to the particular embodiments described and illustrated herein but includes all modifications and variations falling within the scope of the disclosure as defined in the appended embodiments.

Example 1—Biofilm Formation Elimination/Reduction & Inhibition of Bacterial Biofilm Species Found in Wounds A study was performed to evaluate an anti-biofilm activity of a biophotonic composition of the present disclosure on a biofilm generated by a Gram-negative, rod-shaped bacterium, e.g., Pseudomonas aeruginosa or Proteus mirabilis, and a biofilm produced by a Gram-positive coccal bacterium, e.g., Staphylococcus aureus. Each of these bacterial species is a major cause of wound infection and wound-associated biofilm formation.

Specifically, experiments were performed to assess an effect of illumination on the effectiveness of the biophotonic composition to reduce the presence of a wound biofilm and also the presence of the wound-associated bacterial species (see, DeLeon et al. (2014) "Synergistic Interactions of Pseudomonas aeruginosa and Staphylococcus aureus in an In Vitro Wound Model", Infection and Immunity, 82(11): 4718-4728). In addition, experiments were performed to assess the effect of varying an amount of an oxidant (e.g., urea peroxide (UP), also referred to as carbamide peroxide) in the biophotonic composition and the effect of such a variation on the ability of the biophotonic composition to reduce the presence of a wound biofilm and the presence of the wound-associated bacterial species. Illumination of the biophotonic composition was carried out with a multi-LED lamp (THERA™ lamp) emitting non-coherent blue light in a wavelength range of 400 to 470 nm with the lamp placed at a distance of 5 cm from the given biofilm.

Preparation of Bacterial Biofilms

A biofilm of the given bacterial species was prepared in accordance with the methodology published in Javanbakht et al. (2016) "Relating the Surface Properties of Supraparamegnetic Iron Oxide Nanoparticles (SPIONS) to Their Bactericidal Effect towards a Biofilm of Streptococcus mutans" PLOS ONE, 11(4), e0154445. Doi:10.1371/journal.pone.0154445.

Day 1: Bacteria (P. aeruginosa, P. mirabilis, or S. aureus) were inoculated on TYE medium agar plates (diameter of plates: 10 cm) and the plates were incubated overnight in dark at 37° C. to allow for colonies to grow.

Day 2: A sample was prepared containing 5 mL of TYE liquid cultural medium, 25 µL of glucose (40% concentration). A small quantity of bacteria from the plate were inoculated into the liquid media. The liquid sample was incubated overnight at 37° C. overnight in dark.

Day 3: An aliquot of the liquid medium containing overnight culture from day 2 was withdrawn and an absorbance reading was taken of the aliquot to determine whether sufficient bacterial cell growth had occurred in order to proceed. Thereafter, a diluted sample was prepared containing 8.875 mL of cultural medium, 125 µL of saccharose (40%) and 1 mL of the bacterial sample prepared in day 2. 500 µL of the diluted solution of bacteria was distributed in each well of a FCS plate and the plate was left to incubate in the oven at 37° C. overnight.

Day 4: Confocal microscopy was performed on the given bacterial biofilm using a Leica TCS SP5 confocal laser scanning microscope.

Bacterial Cell Counting

The absorbance value of the bacterial cells was determined by a HACH DR 2800 spectrometer (0.84 AU). The concentration of bacterial cells in the liquid TYE culture medium containing 0.2% glucose and incubated for 24 h in the dark at 37° C. was $1.0 \times 10^7$ bacteria per mL (see, Javanbakht et al. (2016)).

Quantification of the Bacteria in the Biofilms

To assess whether a biophotonic composition of the present disclosure could have an anti-biofilm effect, a 120 mg sample of the given composition was placed into the biofilm bearing well on the FCS plate. Prior to adding the composition to the well, the bacteria in the well were quantified. The measured thickness of the biofilms of P. aeruginosa, P. mirabilis, and S. aureus were 7.0 µm and 14.0 µm, respectively. For P. mirabilis only, the BacLight stains were added after the treatment with the biophotonic composition. These biofilm thicknesses are in accordance with biofilms produced by each of these bacterial species as found, for example, in Dong et al. (2015) "Distribution and Inhibition of Liposomes on Staphylococcus aureus and Pseudomonas aeruginosa Biofilm" PLoS ONE 10(6): e0131806. Doi10.1371/journal-pone.0131806. The thickness of the added gels was 1.5 mm.

A BacLight kit (Invitrogen) technique was used to evaluate, by microscopic in situ image analysis, the presence of live and dead bacteria to assess each of the tested compositions' anti-biofilm effect. The methodology utilized was in accordance with that described in Javanbakht et al. (2016), with the live and dead bacteria being stained green and red, respectively, whereas a third image in a set was a merged image of the live and dead cells. Two types of controls were used: the first contained the bacterial cells alone and the second control contained the bacterial cells incubated with the BacLight kit.

Biological Assessment

A confocal fluorescence microscope (Leica TCS SP5) was used for in situ for the biofilms evaluations. As noted above, cell viability was determined with a standard Live/Dead BacLight (Invitrogen) test using SYTO9-propidium iodide. Cell numbers were quantified using a HACH DR 2800 spectrometer using DR2700 software. Biofilms were stained with propidium iodide and Syto 9 for 15 minutes, prior to observation [see, Javanbakht et al. (2016), and also Zhang et al. (2011), "Quantifying Diffusion in a Biofilm of Streptococcus mutans", Antimicrobial Agents and Chemotherapy, 55(3): 1075-1081)] before adding 120 mg of the composition. The experiments for P. aeruginosa, P. mirabilis, or S. aureus were carried out in triplicate and the imaging of samples was carried out fifteen times and the standard deviations of the ratio of dead to total cells were calculated.

Results and Discussion

Quantification of the Bacteria in the Biofilms

Tables 1-4 show the percentages of bacterial mortality in the biofilms of P. aeruginosa, P. mirabilis, or S. aureus as a function of the presence or absence of chromophore, the presence or absence of UP (with varying %), and illumination with the THERA™ lamp

TABLE 1

Percentages of bacterial mortality of *Pseudomonas aeruginosa*.

| Experimental condition | Concentration of UP (%) in gel | Duration of illumination | Increase of bacterial mortality (%) |
|---|---|---|---|
| Gel lacking chromophore | 0 | No illumination | 12.3 ± 2.1 |
| Gel lacking chromophore + carbopol gel | 0 | No illumination | 14.1 ± 1.7 |
| Gel lacking chromophore + carbopol gel | 0 | 5 minutes | 16.4 ± 4.5 |
| Gel with chromophore (Eosin Y at 0.305 mg/ml) + carbopol gel | 0 | No illumination | 21.4 ± 3.4 |
| Gel with chromophore (Eosin Y at 0.305 mg/ml) + carbopol gel | 0 | 5 minutes | 31.9 ± 4.3 |
| Gel with chromophore (Eosin Y at 0.305 mg/ml) + carbopol gel with UP | 1 | No illumination | 24.6 ± 1.5 |
| Gel with chromophore (Eosin Y at 0.305 mg/ml) + carbopol gel with UP | 1 | 5 minutes | 42.5 ± 2.3 |
| Gel with chromophore (Eosin Y at 0.305 mg/ml) + carbopol gel with UP | 3 | No illumination | 31.2 ± 1.9 |
| Gel with chromophore (Eosin Y at 0.305 mg/ml) + carbopol gel with UP | 3 | 5 minutes | 48.4 ± 1.5 |
| Gel with chromophore (Eosin Y at 0.305 mg/ml) + carbopol gel with UP | 6 | No illumination | 35.9 ± 2.4 |
| Gel with chromophore (Eosin Y at 0.305 mg/ml) + carbopol gel with UP | 6 | 5 minutes | 50.5 ± 1.8 |
| Gel with chromophore (Eosin Y at 0.305 mg/ml) + carbopol gel with UP | 12 | No illumination | 49.5 ± 3.5 |
| Gel with chromophore (Eosin Y at 0.305 mg/ml) + carbopol gel with UP | 12 | 5 minutes | 53.7 ± 2.6 |

TABLE 2

Percentages of bacterial mortality of *Staphylococcus aureus*.

| Experimental condition | Concentration of UP (%) | Duration of photo-induction | Increase of bacterial mortality (%) |
|---|---|---|---|
| Gel lacking chromophore | 0 | No illumination | 9.5 ± 2.8 |
| Gel lacking chromophore + carbopol gel | 0 | No illumination | 16.1 ± 2.0 |
| Gel lacking chromophore + carbopol gel | 0 | 5 minutes | 20.9 ± 3.8 |
| Gel with chromophore (Eosin Y at 0.305 mg/ml) + carbopol gel | 0 | No illumination | 22.4 ± 2.8 |
| Gel with chromophore (Eosin Y at 0.305 mg/ml) + carbopol gel | 0 | 5 minutes | 34.2 ± 2.9 |
| Gel with chromophore (Eosin Y at 0.305 mg/ml) + carbopol gel with UP | 1 | No illumination | 30.8 ± 1.3 |
| Gel with chromophore (Eosin Y at 0.305 mg/ml) + carbopol gel with UP | 1 | 5 minutes | 33.6 ± 2.4 |
| Gel with chromophore (Eosin Y at 0.305 mg/ml) + carbopol gel with UP | 3 | No illumination | 32.3 ± 1.7 |
| Gel with chromophore (Eosin Y at 0.305 mg/ml) + carbopol gel with UP | 3 | 5 minutes | 35.5 ± 3.0 |
| Gel with chromophore (Eosin Y at 0.305 mg/ml) + carbopol gel with UP | 6 | No illumination | 34.9 ± 1.8 |
| Gel with chromophore (Eosin Y at 0.305 mg/ml) + carbopol gel with UP | 6 | 5 minutes | 46.9 ± 2.6 |
| Gel with chromophore (Eosin Y at 0.305 mg/ml) + carbopol gel with UP | 12 | No illumination | 38.4 ± 2.6 |
| Gel with chromophore (Eosin Y at 0.305 mg/ml) + carbopol gel with UP | 12 | 5 minutes | 55.6 ± 2.3 |

TABLE 3

Percentages of bacterial mortality of *Proteus mirabilis*

| Gel | Thera ™ Lamp | Average % dead | SD |
|---|---|---|---|
| Control (Set 1) | — | 8.1 | 5.1 |
| Chromo + Carrier UP 0 | 1 min | 36.6 | 19.1 |
| Chromo + Carrier UP 1 | 1 min | 55.4 | 13.5 |
| Chromo + Carrier UP 3 | 1 min | 53.1 | 25.6 |
| Chromo + Carrier UP 6 | 1 min | 48.3 | 27.0 |
| Chromo + Carrier UP 12 | 1 min | 49.3 | 23.6 |
| Control (Set 2) | — | 8.1 | 5.1 |
| Chromo + Carrier UP 0 | 2 min | 49.6 | 18.3 |
| Chromo + Carrier UP 1 | 2 min | 62.1 | 14.7 |
| Chromo + Carrier UP 3 | 2 min | 59.8 | 7.0 |
| Chromo + Carrier UP 6 | 2 min | 52.0 | 16.4 |
| Chromo + Carrier UP 12 | 2 min | 53.8 | 19.0 |
| Control (Set 3) | — | 22.4 | 14.9 |
| Chromo + Carrier UP 0 | 5 min | 62.1 | 26.7 |
| Chromo + Carrier UP 1 | 5 min | 92.1 | 11.7 |
| Chromo + Carrier UP 3 | 5 min | 88.3 | 13.7 |
| Chromo + Carrier UP 6 | 5 min | 92.9 | 9.9 |
| Chromo + Carrier UP 12 | 5 min | 94.6 | 8.2 |
| Control (Set 4) | — | 21.5 | 10.9 |
| Chromo Placebo + Carrier UP 1 | 5 min | 40.0 | 22.6 |
| Chromo Placebo + Carrier UP 3 | 5 min | 36.1 | 25.5 |
| Chromo Placebo + Carrier UP 6 | 5 min | 40.3 | 21.2 |

TABLE 3-continued

Percentages of bacterial mortality of Proteus mirabilis

| Gel | Thera ™ Lamp | Average % dead | SD |
|---|---|---|---|
| Chromo Placebo + | Carrier UP 12 | 5 min | 47.0 | 30.3 |
| Control (Set 5) | — | 10.3 | 5.2 |
| Chromo Placebo+ | Carrier Placebo | 1 | 9.2 | 6.3 |
| Chromo Placebo+ | Carrier Placebo | 3 | 18.6 | 4.9 |
| Chromo Placebo+ | Carrier Placebo | 5 | 20.2 | 21.2 |
| Chromo Placebo+ | Carrier Placebo | 10 | 24.4 | 24.4 |
| Control (Set 6) | — | 12.0 | 5.4 |
| Chromo + | Carrier Placebo | 1 | 22.8 | 4.6 |
| Chromo + | Carrier Placebo | 3 | 31.3 | 13.9 |
| Chromo + | Carrier Placebo | 5 | 45.4 | 43.6 |
| Chromo + | Carrier Placebo | 10 | 32.0 | 12.7 |
| Control (Set 7) | — | 12.0 | 5.4 |
| Chromo + | Carrier UP 12 | 1 | 68.2 | 29.5 |
| Chromo + | Carrier UP 12 | 3 | 79.0 | 10.4 |
| Chromo + | Carrier UP 12 | 5 | 95.2 | 1.2 |
| Chromo + | Carrier UP 12 | 10 | 95.7 | 7.4 |

SD = Standard Deviation;
"Carrier UP 12" indicates carrier gel (carbopol gel) with 12% UP concentration (carrier gel bearing a given % of UP are similarly indicated as such);
"carrier placebo" indicates carrier without UP;
"chromo placebo+" indicates gel with no chromophore.

TABLE 4

Percentages of bacterial mortality for P. mirabilis, P. aeruginosa, and S. aureus

| Gel | Thera ™ Lamp | Average % dead | SD |
|---|---|---|---|
| Control (Set P. mirabilis) | — | 11.8 | 11.0 |
| Chromo + | Carrier UP 12 | — | 33.0 | 30.1 |
| Chromo + | Carrier UP 12 | 5 min | 92.7 | 19.8 |
| Chromo + Placebo | Carrier UP 12 | — | 28.7 | 36.4 |
| Chromo + Placebo | Carrier UP 12 | 5 min | 41.3 | 37.4 |
| Control (Set P. aeruginosa) | — | 40.5 | 19.4 |
| Chromo + | Carrier UP 12 | — | 77.0 | 13.2 |
| Chromo + | Carrier UP 12 | 5 min | 90.1 | 8.2 |
| Chromo + Placebo | Carrier UP 12 | — | 62.1 | 15.2 |
| Chromo + Placebo | Carrier UP 12 | 5 min | 74.9 | 21.0 |
| Control (Set S. aureus) | — | 10.2 | 5.2 |
| Chromo + | Carrier UP 12 | — | 32.5 | 21.1 |
| Chromo + | Carrier UP 12 | 5 min | 92.5 | 4.4 |
| Chromo + Placebo | Carrier UP 12 | — | 16.0 | 11.8 |
| Chromo + Placebo | Carrier UP 12 | 5 min | 21.3 | 14.3 |

As shown in Tables 1 and 2, while there was an increase of the bacterial mortality with the illumination of the non-chromophore/no-UP compositions (compared to the non-illuminated controls), there was a significantly larger increase in the bacterial cell mortality in the presence of the chromophore-containing compositions for both bacterial species, with the mortality being consistently higher in the illuminated test conditions than non-illuminated conditions. Regarding the P. aeruginosa biofilms, the bacterial cell mortality increased when the biophotonic composition contained an increasing amount of UP with a plateau level of 6% UP (although the mortality was still higher with the 12% UP biophotonic gel composition); for the S. aureus biofilms, the biophotonic gel composition with increasing amounts of UP yielded similar results to those of the P. aeruginosa biofilms, both in terms of non-illumination and illuminated test conditions, and with an increasing of the UP concentration with the effect being more pronounced at a 12% UP level. Mortality for P. mirabilis showed similar trends (Table 3). Nevertheless, bacterial mortality for P. aeruginosa, P. mirabilis, and S. aureus was generally higher in the presence of biophotonic gel compositions and illumination, even in the absence of UP (see, generally Tables 1-3). Moreover, confocal microscopy studies showed that biophotonic gel composition combined with 12% UP and illuminated for 5 minutes exerted comparable mortality on S. aureus as 70% ethanol (data not shown). Further, the biophotonic composition with illumination showed reduction in bacterial colonization in venous leg ulcers (data not shown), as determined by MoleculLighti:X™.

Figure 2:
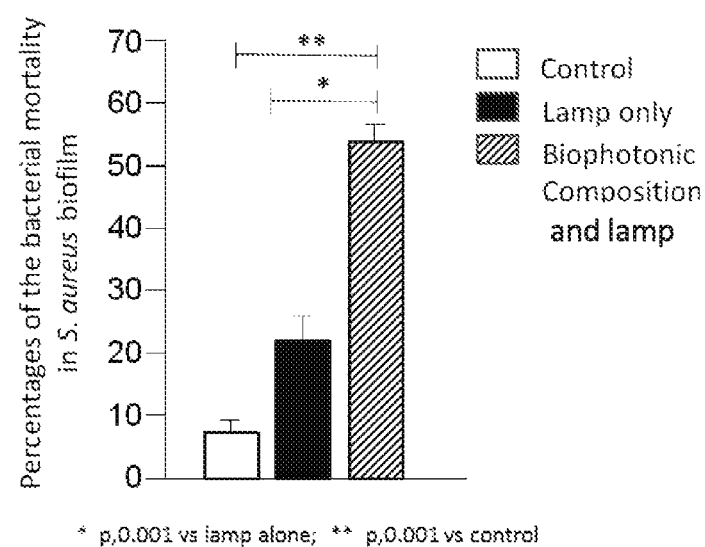
FIG. 2 shows results of the mortality of bacteria *S. aureus* in a biofilm with treatment of a biophotonic composition as disclosed in this application. The *S. aureus* biofilm was treated with a biophotonic composition illuminated in comparison to control composition or illumination alone (illumination in the presence of a composition lacking both the chromophore/oxidant).

As shown in FIG. 1, the effect of treating P. aeruginosa biofilm with a biophotonic composition of the present disclosure, when illuminated, was greater in comparison to treating with either the control composition or just illumination-alone (illumination in the presence of a non-chromophore/no-UP gel). A similar result was observed in the experiment with S. aureus biofilm, with data shown in FIG. 2.

Example 2—Biofilm Reduction/Elimination—Chronic Wounds Treated with a Biophotonic Gel Composition The study was designed to recruit a total of 100 patients at 12 clinical sites, but only 99 patients were included in total in the final analysis. As noted herein, reference is sometimes made to an "interim study" which includes an initial subset of 33 patients for which data were initially available. In certain instances, data from the interim study are disclosed herein.

An initial screen visit to identify eligible patients was conducted prior to beginning treatment. The recruited patients' would be participating for their treatment of chronic wounds (pressure ulcers (PUs), venous leg ulcers (VLUs) and diabetic foot ulcers (DFUs) in a real-life context clinical setting using a biophotonic composition of the present disclosure comprising a synthetic chromophore (Eosin Y) and an oxidant in a carbopol-based gel. For this study, the treatment period was designed to be two applications of the biophotonic composition per week over a period of treatment of 16 weeks for both PUs and VLUs, and over a period of 24 weeks for DFUs. A follow-up period of 8-weeks, commencing upon the termination of treatment, was used to confirm the persistence of wound closure, once a wound has closed.

Patient's ulcer was first cleansed with normal saline. If needed, sharp debridement was performed, to remove excess necrotic tissue or foreign materials. The biophotonic composition was then prepared, and an approximately 2 mm thick layer of the composition was applied on the surface of the ulcer. The patient was then supplied with eye protectors and the persons administering the treatment were requested to wear goggles, to protect their eyes. The KLOX Multi-LED light (THERA™ lamp) delivering non-coherent blue light in a range 400-470 nm was then placed over the wound area, at a measured distance of 5 cm, using the attached lamp measuring probe. The ulcer was illuminated for a period of 5 minutes. Once the illumination period was completed, the composition was removed from the wound surface with a sterile spatula. The wound was then wiped with a moist towel or gauze, and then irrigated with saline solution. A non-adherent dressing was applied, either self-fixating or fixed to the patient with tape and/or bandages, to prevent any contact between the wound and the external environment. Local standard of care was then followed.

Efficacy was assessed using the following endpoints:

Rate of complete wound closure (wound closure being defined as skin re-epithelialization without drainage or dressing requirements confirmed at two consecutive visits, two weeks apart);

Rate of complete wound closure by week 16 for PUs and VLUs, and by week 24 for DFUs;

Time to complete wound closure;

Wound area reduction over time;

Wound volume reduction over time;

Incidence of wound breakdown, following closure;

Impact of treatment on patients' quality of life;

Ease of use by healthcare professionals.

From the one hundred screened patients who enrolled in the study, a total of ninety-nine were enrolled and treated, at least once. Of the thirty-three patients in the interim study, sixteen patients completed the study period as per protocol, while seventeen patients who met the criteria were enrolled and treated, but discontinued early. Among the seventeen patients who early discontinued from the study, eleven were being treated for diabetic foot ulcers (DFUs), two were being treated for pressure ulcers (PUs) and four were being treated for venous leg ulcers (VLUs).

With respect to the demographic and other baseline criteria for the ninety-nine patients of the trial, the mean age of the patients was 68.70 years, with the youngest patient being 38 years-old whereas the oldest patient was 88 years-old. The average age was lower in the PU patient (60.18 years) and DFU patient (69.27 years) groups compared to the patients in the VLU group (70.80 years). Regarding the gender of the thirty-three patients, as shown in Table 5 below, two-thirds of the patients were males and one-third were females.

TABLE 5

| Patients gender - all wounds | | |
|---|---|---|
| Gender | Number of patients | % |
| Male | 67 | 67.7 |
| Female | 32 | 32.3 |
| Total | 99 | 100 |

As shown in Table 6 below, each chronic wound type had representation in both male and female populations for the ninety-nine patients presented in the final analysis.

TABLE 6

| Patients gender - number of patients by type of wound | | | |
|---|---|---|---|
| Gender | PU | DFU | VLU |
| Male | 13 | 25 | 29 |
| Female | 2 | 7 | 23 |
| Total | 15 | 32 | 52 |

Other demographic information for the ninety-nine patients included ethnicity (all ninety-nine were Caucasian), smoking status as of the date of screening (fifty-four never smoked, thirty-eight had stopped smoking, and seven patients were smoker), vital signs including heart rate, blood pressure, body temperature and respiration rate (none of the ninety-nine patients vital signs was considered as clinically significant by the investigators) and body-mass index Among the three different types of chronic ulcers treated in the 99 patients included in the final analysis, staging was assessed by the investigators at the patient's screening visit for PUs and DFUs as shown below in Tables 7 and 8, respectively.

The classification used for pressure ulcers was the staging system proposed by the National Pressure Ulcer Advisory Panel (NPUAP) and the European Pressure Ulcer Advisory Panel (EPUAP). (Source: National Pressure Ulcer Advisory Panel and European Pressure Ulcer Advisory Panel. Pressure Ulcer Treatment. Quick Reference Guide 2009. Available at: http://www.npuap.org). Only Stages II and III Pressure ulcers were accepted in the study. As shown on Table 8 (below), the majority (60%) of the PUs patients enrolled were classified as Stage III at study entry.

TABLE 7

| EPUAP/NPUAP Staging - Pressure Ulcers | | |
|---|---|---|
| Stage | Description | Additional Description |
| STAGE I | Intact skin with nonblanchable redness of a localized area usually over a bony prominence. Darkly pigmented skin may not have visible blanching; its color may differ from the surrounding area. | The area may be painful, firm, soft, warmer or cooler as compared to adjacent tissue. Stage I may be difficult to detect in individuals with dark skin tones. May indicate "at risk" persons (a heralding sign of risk). |

TABLE 7-continued

EPUAP/NPUAP Staging - Pressure Ulcers

| Stage | Description | Additional Description |
|---|---|---|
| STAGE II | Partial thickness loss of dermis presenting as a shallow open ulcer with a red pink wound bed, without slough. May also present as an intact or open/ruptured serum-filled blister. | Presents as a shiny or dry shallow ulcer without slough or bruising*. This stage should not be used to describe skin tears, tape burns, perineal dermatitis, maceration or excoriation. *Bruising indicates suspected deep tissue injury. |
| STAGE III | Full thickness tissue loss. Subcutaneous fat may be visible but bone, tendon or muscle are not exposed. Slough may be present but does not obscure the depth of tissue loss. May include undermining and tunneling. | The depth of a Stage III pressure ulcer varies by anatomical location. The bridge of the nose, ear, occiput and malleolus do not have subcutaneous tissue and Stage III ulcers can be shallow. In contrast, areas of significant adiposity can develop extremely deep Stage III pressure ulcers. Bone/tendon is not visible or directly palpable. |
| STAGE IV | Full thickness tissue loss with exposed bone, tendon or muscle. Slough or eschar may be present on some parts of the wound bed. Often include undermining and tunneling. | The depth of a Stage IV pressure ulcer varies by anatomical location. The bridge of the nose, ear, occiput and malleolus do not have subcutaneous tissue and these ulcers can be shallow. Stage IV ulcers can extend into muscle and/or supporting structures (e.g., fascia, tendon or joint capsule) making osteomyelitis possible. Exposed bone/tendon is visible or directly palpable. |
| UNSTAGEABLE | Full thickness tissue loss in which the base of the ulcer is covered by slough (yellow, tan, gray, green or brown) and/or eschar (tan, brown or black) in the wound bed. | Until enough slough and/or eschar is removed to expose the base of the wound, the true depth, and therefore stage, cannot be determined. Stable (dry, adherent, intact without erythema or fluctuance) eschar on the heels serves as "the body's natural (biological) cover" and should not be removed. |

The classification used for DFUs was the University of Texas classification. The University of Texas system assesses ulcer depth, the presence of wound infection, and the presence of clinical signs of lower-extremity ischemia. This system uses a matrix of grade on the horizontal axis and stage on the vertical axis. Only Diabetic foot ulcers with Stages 1A (superficial, non-infected, non-ischemic wound not involving tendon, capsules, or bone) or 2A (non-infected, non-ischemic wound penetrating to tendon or capsule but not in the bone or joint) were accepted. As shown on Table 11 (below), the majority (56.3%) of the DFUs enrolled were of Stage 2A.

TABLE 8

University of Texas Staging- Diabetic Foot Ulcers

| | 0 | 1 | 2 | 3 |
|---|---|---|---|---|
| A | Pre- or post-ulcerative site that has healed | Superficial wound not involving tendon, capsule, or bone | Wound penetrating to tendon or capsule | Wound penetrating bone or joint |
| B | With infection | With infection | With infection | With infection |
| C | With ischemia | With ischemia | With ischemia | With ischemia |
| D | With infection and ischemia | With infection and ischemia | With infection and ischemia | With infection and ischemia |

No classification was used for VLUs due to the lack of standardized staging internationally recognized.

For the ninety-nine patients presented in the study, Table 9 presents a breakdown with respect to chronic wound type of the patients; the majority of the patients were of either the DFU or VLU groups.

TABLE 9

Type of wounds included in the final analysis

| Wound Type | Number of patients | Percentage of patients |
|---|---|---|
| DFU | 32 | 33.3% |
| PU | 15 | 15.2% |
| VLU | 52 | 52.5% |
| Total Number of Patients | 99 | 100% |

The staging of the wounds for the PU and DFU patients presented in the final analysis is provided in Table 10 and Table 11, respectively.

TABLE 10

Pressure Ulcers' Staging at Screening

| Stage | Number of patients | % |
|---|---|---|
| II | 6 | 40.0 |
| III | 9 | 60.0 |
| Total | 15 | 100 |

TABLE 11

Diabetic Foot Ulcers' Staging at Screening

| Stage | Number of patients | % |
|---|---|---|
| 1A | 14 | 43.8 |
| 2A | 18 | 256.3 |
| Total | 32 | 100 |

Given that the study was an observational study in real-life conditions, age of the wounds was not part of the eligibility criteria thereby explaining degree of variation from one wound to another when comparing patient-to-patient for the chronic wound type.

On average, the duration of the chronic ulcers (PUs, DFUs and VLUs combined) at screening for the study was 35.5 months. Average chronic ulcers duration was 64.1 months for PUs, 424.9 months for VLUs and 10.2 months for DFUs. The youngest ulcer had happened just prior to the patient's enrollment (PU) whereas the oldest ulcer was approximately 52 years old (VLU). Table 12 below presents a summary (all wounds combined), while Table 13 presents a summary specifically for the (PU patients, Table 14 presents a summary for the DFU patients and Table 15 presents a summary for the VLU patients.

TABLE 12

Chronic ulcers duration at baseline (including PUs, DFUs, and VLUs)

| Average (months) | S.D. (months) | Minimum (months) | Maximum (months) |
|---|---|---|---|
| 35.5 | 92.8 | 0.0 | 625.3 |

Note:
N = 99.
Duration calculated from date of wound diagnosis to date of screening, as reported by patients.
S.D.: Standard Deviation

TABLE 13

Pressure ulcers duration at screening

| Average (months) | S.D. (months) | Minimum (months) | Maximum (months) |
|---|---|---|---|
| 42.1 | 158.5 | 0.0 | 625.3 |

Note:
N = 15.
Duration calculated from date of wound diagnosis to date of screening, as reported by patients.
S.D.: Standard Deviation.

TABLE 14

Diabetic foot ulcers duration at screening

| Average (months) | S.D. (months) | Minimum (months) | Maximum (months) |
|---|---|---|---|
| 10.2 | 14.7 | 0.0 | 72.5 |

Note:
N = 32.
Duration calculated from date of wound diagnosis to date of screening, as reported by patients.
S.D.: Standard Deviation.

TABLE 15

Venous leg ulcers duration at screening

| Average (months) | S.D. (months) | Minimum (months) | Maximum (months) |
|---|---|---|---|
| 424.9 | 93.9 | 0.0 | 518.0 |

Note:
N = 52.
Source: Duration calculated from date of wound diagnosis to date of screening, as reported by patients.
S.D.: Standard Deviation.

Further characteristics of the chronic wound type that each of the ninety-nine patients presented in the final analysis were suffering from included the area of skin and soft tissues that the given patient's wound encompassed and the bodily location of the wound. The size of the chronic ulcers was on average 10.96 cm$^2$ at the Screening visit, varying from 0.1 cm$^2$ up to 52.2 cm$^2$. The median size (all wounds combined) at study entry was 8.85 cm$^2$ (see Table 16).

TABLE 16

Chronic ulcers (all types) areas at screening and First Treatment Visit

| Average (cm$^2$) | S.D. (cm$^2$) | Minimum (cm$^2$) | Maximum (cm$^2$) |
|---|---|---|---|
| 7.39 | 9.47 | 0.1 | 52.50 |

Note:
N = 99.
S.D.: Standard Deviation.

The size of the chronic wound varied between the three chronic wound types, with DFUs presenting the smallest average size and VLUs presenting the largest average size at both the Screening and the First Treatment Visit time points. Wound size data for patients with PU, DFU, or VLU were presented in Tables 17, 18, and 19, respectively.

TABLE 17

Pressure ulcers areas at Screening and First Treatment Visit

| Average ($cm^2$) | S.D. ($cm^2$) | Minimum ($cm^2$) | Maximum ($cm^2$) |
|---|---|---|---|
| 4.29 | 5.36 | 0.1 | 21.30 |

Note:
N = 15.
S.D.: Standard Deviation.

TABLE 18

Diabetic foot ulcers areas at Screening and First Treatment Visit

| Average ($cm^2$) | S.D. ($cm^2$) | Minimum ($cm^2$) | Maximum ($cm^2$) |
|---|---|---|---|
| 3.03 | 3.4 | 0.1 | 12.30 |

Note:
N = 32.
S.D.: Standard Deviation.

TABLE 19

Venous leg ulcers areas at Screening and First Treatment Visit

| Average ($cm^2$) | S.D. ($cm^2$) | Minimum ($cm^2$) | Maximum ($cm^2$) |
|---|---|---|---|
| 10.96 | 11.39 | 0.3 | 52.5 |

Note:
N = 52.
S.D.: Standard Deviation

The bodily location of the chronic wounds in each of the three patient groups, at the final analysis (ninety-nine patients) varied between patients in the given group. The wound locations for the PU patients, the DFU patients and the VLU patients in the final analysis are presented in Tables 20, 21 and 22, respectively.

TABLE 20

Pressure ulcers location

| Pressure Ulcers Wound Location | Total Number of Wounds |
|---|---|
| Thigh | 1 |
| Sacrum/buttock | 9 |
| Heel | 5 |
| Total | 15 |

Note:
N = 15.

TABLE 21

Diabetic foot ulcers location

| Diabetic foot ulcers Wound Location | Total Number of Wounds |
|---|---|
| 1st Dorsal Toe | 2 |
| 1st Plantar Toe | 4 |
| $4^{th}$ Plantar Toe | 1 |
| Ankle | 5 |
| Arch of Foot | 2 |
| Ball of Foot | 13 |
| Dorsal Foot | 1 |
| Heel | 4 |
| Total | 32 |

Note:
N = 32.

TABLE 22

Venous leg ulcers location

| Venous leg ulcers Wound Location | Total Number of Wounds |
|---|---|
| External left ankle | 6 |
| External left leg | 2 |
| External right ankle | 7 |
| External right calf | 4 |
| External right leg | 3 |
| Internal left ankle | 12 |
| Internal left leg | 1 |
| Internal right ankle | 9 |
| Internal right calf | 3 |
| Internal right leg | 3 |
| External left calf | 1 |
| Internal left calf | 1 |
| Total | 52 |

Note:
N = 52.

All of the chronic ulcers treated in the study had failed on at least one form of treatment before. Overall, the vast majority had been previously treated with dressings and debridement, as per standard of care and clinical practice guidelines, with a complete list of prior treatments being presented in Tables 23 (all wounds), Table 24 (for the PU patients), Table 25 (for the DFU patients), and Table 26 (for the VLU patients). Dressings and medicated dressings were the most frequent treatments mentioned. Thirteen DFU patients had also already received systemic antibiotics, and fourteen VLU patients had a history of failed skin graft.

TABLE 23

Ulcers' prior treatments (all wounds combined)

| Description | Number of patients |
|---|---|
| Topical antibiotics | 7 |
| Compression (bands, socks) | 3 |
| Dressings (dry, wet, gels) | 26 |
| Medicated dressings | 102 |
| Systemic antibiotics | 6 |
| Topical disinfectants (including topical ointments) | 9 |
| Debridement | 14 |
| Grafting | 44 |
| Offloading | 1 |
| Collagen | 13 |
| Negative Pressure Wound Therapy | 3 |

Note:
N = 99. Patients might have more than one treatment.

TABLE 24

Pressure ulcers' prior treatments

| Description | Number of patients |
| --- | --- |
| Topical antibiotics | 2 |
| Dressings (dry, wet, gels) | 0 |
| Medicated dressings | 7 |
| Systemic antibiotics | 1 |
| Topical disinfectants | 2 |
| Topical Ointments | 3 |
| Debridement | 1 |
| Grafting | 0 |

Note:
N = 15. Patients might have more than one treatment.

TABLE 25

Diabetic foot ulcers' prior treatments

| Description | Number of patients |
| --- | --- |
| Topical antibiotics | 4 |
| Compression (bands, socks) | 0 |
| Dressings (dry, wet, gels) | 5 |
| Medicated dressings | 20 |
| Systemic antibiotics | 4 |
| Topical disinfectants | 4 |
| Grafting | 1 |
| Offloading | 1 |

Note:
N = 32. Subjects might have more than one treatment.

TABLE 26

Venous leg ulcers' prior treatments

| Description | Number of patients |
| --- | --- |
| Topical antibiotics | 3 |
| Compression (bands, socks) | 3 |
| Dressings (dry, wet, gels) | 21 |
| Medicated dressings | 75 |
| Systemic antibiotics | 1 |
| Topical disinfectants | 1 |
| Topical Ointments | 2 |
| Debridement | 13 |
| Grafting | 13 |
| Collagen | 13 |
| Negative Pressure Wound Therapy | 3 |

Note:
N = 52.

Patient compliance to study visits from Screening to the end of study, was to be considered as excellent, which is not always evident as compliance may sometimes be an issue with patients affected by chronic wounds. Overall, 95.2% of study treatment visits planned by the protocol were received during the treatment period.

With respect to the length of time that the patients were under investigational treatment, on average, patients were under investigational treatment for 80.45 days. The shortest period treatment was days, for one of the DFU patients, whereas the longest treatment period was 224 days for four of the VLU patients. Table 27 presents the overall data for the ninety-nine patients' duration of investigational treatment.

TABLE 27

Investigational treatment duration

| Average treatment duration (days) | Standard deviation (days) | Minimum duration (days) | Maximum duration (days) |
| --- | --- | --- | --- |
| 80.45 | 51.18 | 0.0 | 224.0 |

Note:
N = 99.

The duration of investigational treatment varied depending on the chronic wound type group, and as shown in Table 28, the number of treatment days in the VLU group was lower than in the groups of PU and VLU. It might be explained by the high rate of wound closure in the VLU group, and by the fact that these wounds responded overall quickly and favourably to the study treatment.

TABLE 28

Investigational treatment duration, by type of wound

| Type of wound | Average treatment duration (days) | Standard deviation (days) | Minimum duration (days) | Maximum duration (days) |
| --- | --- | --- | --- | --- |
| PU | 87.53 | 37.14 | 19 | 142 |
| DFU | 70.28 | 66.6 | 0 | 224 |
| VLU | 84.67 | 43.13 | 3 | 173 |

Note:
N = 99. Average of all wounds shown in Table 27.

A majority of the thirty-three patients comprising the interim analysis of the study responded positively to the treatment with the biophotonic composition; a total of twenty-one of the patients were considered to be full responders, wherein a full responder was defined as having a decrease of the wound size area of more than 90% at the end of the study period and/or decrease of more than 50% of the size in 15 days or less. This cohort of full responders comprised twelve DFU patients, eight VLU patients and one PU patient.

Furthermore, three patients in each of DFU and VLU wound types were considered to be partial responders, wherein a partial responder was defined s having a decrease of the size of the wound during the study period, but without meeting the criteria of full responder. Nine of the full responder DFU patients experienced a total closure of their wounds by the end of their participation in the study, while seven of the eight VLU experienced full closure by the end of their participation (with the eighth full responder VLU experiencing a 97% decrease in wound area by this patients end of participation).

The full responder PU patient, with this patient experienced a complete wound closure by the day of their last treatment visit (day 47). Overall, of the thirty-three patients presented in the interim analysis, 16 patients (48.5% of the total number of patients) experienced a full closure of their wound totally during the study period, and the mean time to reach total closure was 46.8 days. This mean time varied depending on the type of wound; it was lower for DFUs (mean time of 37.2 days), whereas it was higher for PUs (47.0 days) and VLUs (53.6 days). Of the three partial responders in the VLU cohort, two of these patients' wounds were graft-ready by their completion of the study, and for the three partial responders in the DFU patient cohort, one of these patients' wound was graft ready by the end of the patient's participation in the study.

In the ninety-nine patient study, the average number of treatments by types of wounds are (i) 23.90 treatments for patients with VLU, (ii) 18.31 treatments for patients with DFU, and (iii) 23.40 treatments for patients with PU. Significant variations of the wound size area as compared to baseline were found for VLU (p<0.001) and DFU (p=0.001). In the study, 47 wounds closed completely during the study period, especially VLUs (26) and DFUs (17). It represents 47.5% of the wounds treated during the study period. By type of wounds, the results are (i) 50% of the VLU wounds closed completely; (ii) 50% of the DFU wounds closed completely; and (iii) 33.3% of the PU wounds closed completely.

Looking at the trajectories of relative wound area regression over time, superior results were obtained with VLUs and DFUs, showing similar results. The mean time to reach a regression of 50% of the wound area was approximately 8 weeks for VLUs and 3.5 weeks for DFUs.

Wound breakdown (dehiscence) was assessed at least two weeks after confirmation of wound closure through the observations performed during the follow-up period. This phase of the study was specifically designed to allow the documentation of the wound closure persistence based on the definition of wound closure being "wound closure is defined as skin re-epithelialization without drainage or dressing requirements confirmed at two consecutive visits, two weeks apart"). Incidence of wound breakdown was assessed at two timepoints during the follow-up period:

after the two-week evaluation period following wound closure: two wounds (5.13%) had a wound breakdown (N=39);

after the eight-week evaluation period following wound closure: two wounds (5.71%) had a wound breakdown (N=35).

These low percentages of wound breakdown show that, when a chronic wound totally closed following treatment, 95% of them remain totally closed after the two-week follow-up period, and even after the eight-week follow-up period.

This low incidence of wound breakdown at two weeks and eight weeks' post-closure confirms the efficacy profile and long-lasting action of a biophotonic composition of the present disclosure on wound closure.

From the 47 wounds that closed completely, four wounds closed at the last study visit and it was therefore not possible to confirm the absence of wound breakdown for these wounds. Thirty-four wounds were reassessed at Follow-up visit 1 (two weeks following wound closure) and 35 at Follow-up visit 3 (8 weeks following wound closure). During these visits, only two wounds reopened, meaning a rate of wound breakdown after 8 weeks of 5%.

Table 29 presents the results of the wound breakdown.

TABLE 29

Wound breakdown investigation for closed wounds

| Wound type | Closed wounds | Wound breakdown at two weeks (N = 34) | Wound breakdown at eight weeks (N = 35) |
| --- | --- | --- | --- |
| VLU | 26 | 0 | 1 (0603) |
| DFU | 17 | 0 | 1 (1310) |
| PU | 4 | 0 | 0 |
| All wounds | 47 | 0 | 2 |

Note:
N = 47.

Even if a wound was not closed, it was of interest to know if the wound bed was prepared enough to receive a skin graft. For this purpose, a specific question was added in the study questionnaire for ulcer assessment. The results in terms of wound bed preparation were also positive in this study. Investigators were asked to assess regularly during the study period if the wounds became ready to skin graft. Even if the wounds had a profile of hard to heal non responsive wounds at study entry, with a high rate of prognosis factors of poor healing, more than two thirds of the VLU (69.2%) and DFU (68.8%) wounds became ready to skin graft at one point during the study period. Table 30 presents these different data by type of wound, and overall. An estimate of the mean and median age to become graft ready was estimated for each type of wound using the Kaplan-Meir method. Overall, mean time was 95.7 days and median time 86.0 days, but with a significant difference between the wounds. The fastest were the DFUs (mean time of 79.0 days and median time of 41.0 days), followed by VLUs and then by PUs.

TABLE 30

Number of wounds becoming "Graft ready", after initiation of the treatment with the biophotonic composition - summary by type of wound

| | Ready for graft (invest opinion) | | | | | |
| --- | --- | --- | --- | --- | --- | --- |
| | Yes | | No | | Total | |
| Wound type | N | % | N | % | N | % |
| VLU | 36 | 69.2% | 16 | 30.8% | 52 | 100.0% |
| DFU | 22 | 68.8% | 10 | 31.3% | 32 | 100.0% |
| PU | 6 | 40.0% | 9 | 60.0% | 15 | 100.0% |
| All wounds | 64 | 64.6% | 35 | 35.4% | 99 | 100.0% |

Note:
N = 99.

Local clinical signs of wound colonization over time:

Investigators were asked at the first Treatment visit to assess different aspects of the wound and peri-wound skin, including the presence of local signs of colonization or infection (Redness, Pain, Heat, Pus and Swelling). This assessment, which is generally considered as a sign of inflammation, was carried out at the first treatment visit and at every study treatment.

General characteristics at first treatment visit were:
As expected with these hard to heal chronic wounds, the majority of them had local clinical signs of bacterial colonization at study entry, with redness (37.4% all wounds combined) and heat (7.1%). It concerned especially VLU, with 57.7% having redness and 11.5% having heat. There was no clinical sign of bacterial colonization for DFUs and PUs;

This hypothesis of a probable colonization of some of the wounds at study entry is reinforced by the amount of exudate: 26.9% of high exudate level for VLUs and 20.0% for DFUs (18.2% overall);

The great majority (98.0%) had no visible presence of pus.

A fast regression of these clinical signs of bacterial colonization was observed as soon as Week 4:
Redness: from 58% to 36%;
Pain: from 52% to 16%;
Swelling: from 29% to 14%;
No more wound with pus.

Complete results of these different assessments at the first treatment visit are presented in the table below.

TABLE 31

Local signs of colonization/Infection by wound type at 1st Treatment Visit

| | | Wound type | | | | | | |
|---|---|---|---|---|---|---|---|---|
| | | VLU | | DFU | | PU | | Total |
| | | N | % | N | % | N | % | N | % |
| Redness | YES | 30 | 57.7% | 6 | 18.8% | 1 | 6.7% | 37 | 37.4% |
| | NO | 22 | 42.3% | 26 | 81.3% | 14 | 93.3% | 62 | 62.6% |
| | Total | 52 | 100.0% | 32 | 100.0% | 15 | 100.0% | 99 | 100.0% |
| Pain | YES | 27 | 51.9% | 1 | 3.1% | 0 | 0.0% | 28 | 28.3% |
| | NO | 25 | 48.1% | 31 | 96.9% | 15 | 100.0% | 71 | 71.7% |
| | Total | 52 | 100.0% | 32 | 100.0% | 15 | 100.0% | 99 | 100.0% |
| Heat | YES | 6 | 11.5% | 1 | 3.1% | 0 | 0.0% | 7 | 7.1% |
| | NO | 46 | 88.5% | 31 | 96.9% | 15 | 100.0% | 92 | 92.9% |
| | Total | 52 | 100.0% | 32 | 100.0% | 15 | 100.0% | 99 | 100.0% |
| Pus | YES | 1 | 1.9% | 1 | 3.1% | 0 | 0.0% | 2 | 2.0% |
| | NO | 51 | 98.1% | 31 | 96.9% | 15 | 100.0% | 97 | 98.0% |
| | Total | 52 | 100.0% | 32 | 100.0% | 15 | 100.0% | 99 | 100.0% |
| Swelling | YES | 15 | 28.8% | 3 | 9.4% | 3 | 20.0% | 21 | 21.2% |
| | NO | 37 | 71.2% | 29 | 90.6% | 12 | 80.0% | 78 | 78.8% |
| | Total | 52 | 100.0% | 32 | 100.0% | 15 | 100.0% | 99 | 100.0% |

Note:
N = 99.

As was determined previously for the interim analysis, no case of wound infection was observed in DFU patients among the 17 subjects included in the interim analysis. Additionally, no DFU wound required a local or systemic antimicrobial therapy during the interim study period. As mentioned in literature (Lavery et al. (2006), "The efficacy and safety of Grafix(®) for the treatment of chronic diabetic foot ulcers: results of a multi-centre, controlled, randomised, blinded, clinical trial." International Wound Journal, 11(5): 554-60), foot infections occur frequently in individuals with diabetes, with the well-known risk of lower-extremity amputations (infected foot wounds precede two-thirds of lower-extremity amputations, according to Lavery et al., 2006). Wound infections are also responsible of delayed wound healing and wound breakdowns.

This very low number of wound infections throughout the final study period is in favour of an action of the treatment on control of the wound biofilm.

While preferred embodiments of the disclosure have been described above and illustrated in the accompanying drawings, it will be evident to those skilled in the art that modifications may be made therein without departing from the essence of this disclosure. Such modifications are considered as possible variants comprised in the scope of the subject matter of this disclosure.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

The invention claimed is:

1. A method for inhibiting biofilm formation, or disrupting existing or developing biofilms in a subject, comprising:
   a) topically applying a composition comprising at least one xanthene derivative dye and a pharmaceutically acceptable carrier; and
   b) illuminating said composition with actinic light, thereby inhibiting biofilm formation, or disrupting existing or developing biofilms in the subject.

2. The method according to claim 1, wherein the composition is a biophotonic composition.

3. The method according to claim 1, wherein the at least one xanthene derivative dye is selected from the group consisting of eosin, erythrosine, fluorescein, phloxine B, rose bengal, and merbromine.

4. The method according to claim 1, wherein at least one xanthene derivative dye is eosin Y or eosin B.

5. The method according to claim 1, wherein at least one xanthene derivative dye is eosin Y.

6. The method according to claim 1, wherein at least one xanthene derivative dye is erythrosine B.

7. The method according to claim 1, wherein the at least one xanthene derivative dye is present in an amount of from about 0.02% to about 8% by weight of the composition.

8. The method according to claim 1, wherein the at least one xanthene derivative dye is present in an amount of from about 0.5% by weight of the composition.

9. The method according to claim 1, wherein the composition further comprises at least one healing factor.

10. The method according to claim 9, wherein the healing factor is selected from the group consisting of hyaluronic acid, glucosamine, and allantoin.

11. The method according to claim 1, wherein said composition is illuminated with actinic light for at least one treatment period of from about 1 minute to about 9 minutes per $cm^2$ of an area to be treated.

12. The method according to claim 1, wherein said composition is illuminated with actinic light for at least one treatment period of from about 2 minutes to about 8 minutes per $cm^2$ of an area to be treated.

13. The method according to claim 1, wherein said composition is illuminated with actinic light for at least two treatment periods, each period followed by a resting interval.

14. The method according to claim 1, wherein said composition is illuminated with at least two consecutive treatment periods of actinic light wherein each treatment period is from about 1 minute to about 5 minutes per $cm^2$ of an area to be treated, wherein each treatment period is followed by a resting interval for about 1 minute to about 5 minutes.

15. The method according to claim 1, further comprising:
   a) topically applying the composition to the subject's area of biofilm;
   b) illuminating the subject's area of biofilm with actinic light for a period of from about 1 minute to about 10 minutes;
   c) removing the source of actinic light away from the subject's area of biofilm treated for a period of from about 1 minute to about 5 minutes;

d) illuminating the subject's area of biofilm with actinic light for a second time period of from about 1 minute to about 10 minutes; and wherein the first illumination of actinic light activates the composition.

16. The method according to claim 1, wherein the biofilm is associated with at least one of the subject's skin and the subject's soft tissues, and comprises at least one of *Staphylococcus aureus, Pseudomonas aeruginosa*, and *Proteus mirabilis*.

17. The method according to claim 1, wherein the biofilm comprises one of gram-negative bacteria and gram-positive bacteria.

18. The method according to claim 1, wherein the biofilm comprises a gram-positive bacteria.

19. The method according to claim 1, wherein the biofilm is associated with wounds, venous leg ulcer (VLU), diabetic foot ulcer (DFU), or pressure ulcer (PU).

* * * * *